(12) United States Patent
Uesaka et al.

(10) Patent No.: US 9,848,783 B2
(45) Date of Patent: Dec. 26, 2017

(54) BLOOD PRESSURE MEASUREMENT DEVICE

(75) Inventors: Chisato Uesaka, Kyoto (JP); Tomohiro Kukita, Amsterdam (NL); Koji Maruta, Joyo (JP); Kohei Takeoka, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 606 days.

(21) Appl. No.: 13/175,104

(22) Filed: Jul. 1, 2011

(65) Prior Publication Data

US 2012/0004558 A1 Jan. 5, 2012

Related U.S. Application Data

(63) Continuation of application No. PCT/JP2009/070588, filed on Dec. 9, 2009.

(30) Foreign Application Priority Data

Jan. 7, 2009 (JP) ................................ 2009-001819

(51) Int. Cl.
*A61B 5/02* (2006.01)
*A61B 5/0225* (2006.01)
*A61B 5/022* (2006.01)
*A61B 5/021* (2006.01)
*A61B 5/00* (2006.01)

(52) U.S. Cl.
CPC .......... *A61B 5/0225* (2013.01); *A61B 5/7435* (2013.01); *A61B 5/021* (2013.01); *A61B 5/022* (2013.01); *A61B 5/6824* (2013.01)

(58) Field of Classification Search
CPC .......... A61B 8/04; A61B 5/021; A61B 5/022; A61B 5/0225; A61B 5/7435
USPC ......................... 600/301, 481, 485, 491–499
See application file for complete search history.

(56) References Cited

U.S. PATENT DOCUMENTS

| 4,995,399 A | 2/1991 | Hayashi et al. |
| 2005/0171442 A1 | 8/2005 | Shirasaki et al. |
| 2007/0038128 A1* | 2/2007 | Sawanoi et al. ............... 600/485 |
| 2007/0038129 A1* | 2/2007 | Kishimoto et al. ........... 600/485 |

(Continued)

FOREIGN PATENT DOCUMENTS

| JP | H05-32082 U | 8/1993 |
| JP | 2005-218492 A | 8/2005 |

(Continued)

OTHER PUBLICATIONS

International Search Report issued in PCT/JP2009/070588 dated Feb. 2, 2010, and English translation thereof, 4 pages.

(Continued)

*Primary Examiner* — Puya Agahi
(74) *Attorney, Agent, or Firm* — Osha Liang LLP

(57) ABSTRACT

Average blood pressure data of a morning time zone of every week and average blood pressure data of a night time zone of every week calculated by an average calculation portion are stored in a memory by performing blood pressure measurement. An every-week processing portion alternately switches and displays the average blood pressure data of the morning time zone and the average blood pressure data of the night time zone read from the memory based on an instruction input through an operation unit on a display unit every three seconds, or the like.

7 Claims, 22 Drawing Sheets

(56) References Cited

U.S. PATENT DOCUMENTS

2007/0038132 A1* 2/2007 Kishimoto et al. ........... 600/490
2007/0239040 A1* 10/2007 Takeoka et al. .............. 600/485
2009/0062664 A1* 3/2009 Chang et al. ................. 600/485

FOREIGN PATENT DOCUMENTS

JP  3117970 U  1/2006
JP  2007-050016 A  3/2007

OTHER PUBLICATIONS

Patent Abstracts of Japan, Publication No. 2007-050016, Publication Date: Mar. 1, 2007, 1 page.
Patent Abstracts of Japan, Publication No. 2005-218492, Publication Date: Aug. 18, 2005, 1 page.

* cited by examiner (12)

BLOOD PRESSURE MEASUREMENT DEVICE

TECHNICAL FIELD

The present invention relates to blood pressure measurement devices, and in particular, to a blood pressure measurement device for switching and displaying the blood pressure measurement result in response to the operation.

BACKGROUND ART

The blood pressure is desirably measured in the morning (after waking up) and at night (before going to sleep). In recent years, early morning high blood pressure that increases the cardiovascular risk among the high blood pressure is given attention. The early morning high blood pressure is when the blood pressure after waking up (morning) is particularly high. The type of medicine to take differs depending on whether the blood pressure is high only in the morning. Therefore, it is considered effective to find the early morning high blood pressure, and compare the blood pressure values in the morning (after waking up) and at night (before going to sleep) to receive an appropriate treatment.

The conventional technique related to comparing the blood pressure includes the following.

In a device where the respective blood pressure value is displayed when a morning average or night average button of the sphygmomanometer is pushed, a function in which the display transitions to the average value one week before, the average value two weeks before, the average value three weeks before, . . . every time the button is pushed if the morning average (night average) button is continuously pushed is provided (this is referred to as technique 1).

Patent document 1 (Japanese Registered Utility Model Publication No. 3117970) discloses a configuration of alternately displaying the blood pressure value, the pulse rate, and the like to reduce the operation procedure (this is referred to as technique 2).

Patent Document 1: Japanese Registered Utility Model Publication No.

SUMMARY OF INVENTION

Regarding technique 1 described above, the button needs to be pushed two or more times when comparing the morning average and the night average of the same week, and thus, the operation procedure increases. The measurement value in the morning and the measurement value at night cannot be compared unless intended, and the user who does not know the importance of comparison may not notice. Regarding technique 2, the display space can be saved by alternate displaying, but the blood pressure values cannot be compared because the data (e.g., blood pressure value) of the same category are not alternately displayed.

Therefore, one or more embodiments of the present invention provides a blood pressure measurement device for displaying a blood pressure value in a mode that easily enables the comparison of values.

According to one or more embodiments of the present invention, a blood pressure measurement device includes a cuff to be attached to a measurement site of a living body; a control unit for calculating a blood pressure while adjusting pressure of the cuff for blood pressure measurement; a storage unit for storing morning blood pressure data for a plurality of weeks measured in a time zone corresponding to morning and night blood pressure data for a plurality of weeks measured in a time zone corresponding to night calculated by the control unit; a display unit; a display operation unit operated to input instruction related to display using the display unit; and a display processing unit for reading out data from the storage unit and displaying the read data on the display unit.

The morning blood pressure data of each week indicates an average of the data of the blood pressure measured in the time zone corresponding to the morning of the relevant week, and the night blood pressure data of each week indicates an average of the data of the blood pressure measured in the time zone corresponding to the night of the relevant week.

The display processing unit includes a week display processing portion of reading out the morning blood pressure data and the night blood pressure data of a predetermined week from the storage unit when the instruction is input through the display operation unit, and alternately and repeatedly displays the read morning blood pressure data and the night blood pressure data.

The week display processing portion reads the morning blood pressure data and the night blood pressure data of a week of next order with respect to the blood pressure data of the week being displayed from the storage unit when the instruction is input through the display operation unit while alternately and repeatedly displaying the morning blood pressure data and the night blood pressure data and alternately and repeatedly displays the read morning blood pressure data and the night blood pressure data of the week of the next order.

According to one or more embodiments of the present invention, the display processing unit displays information indicating that a blood pressure value of the morning blood pressure data corresponds to a predetermined blood pressure section on the same screen as a display screen of the morning blood pressure data when displaying the morning blood pressure data.

According to one or more embodiments of the present invention, the display processing unit displays information indicating that a blood pressure value of the morning blood pressure data corresponds to the predetermined blood pressure section on the same screen as a display screen of the night blood pressure data when displaying the night blood pressure data.

According to one or more embodiments of the present invention, the display processing unit performs simultaneously display by a rectangular bar sectionalized by a plurality of segments of a predetermined unit and display by numerical values at the same screen of the display unit for a blood pressure indicated by the blood pressure data.

A criterion value indicating the predetermined blood pressure section is displayed in association at a position indicating a blood pressure value corresponding to the criterion value on the bar.

According to one or more embodiments of the present invention, the predetermined blood pressure section refers to section of early morning high blood pressure.

According to one or more embodiments of the present invention, the blood pressure value can be displayed in a mode that enables the values to be easily compared because the display processing unit alternately switches and displays the morning blood pressure data and the night blood pressure data read from the storage unit on the display unit for every predetermined time based on the instruction input through the display operation unit.

DETAILED DESCRIPTION OF INVENTION

Figure 1:
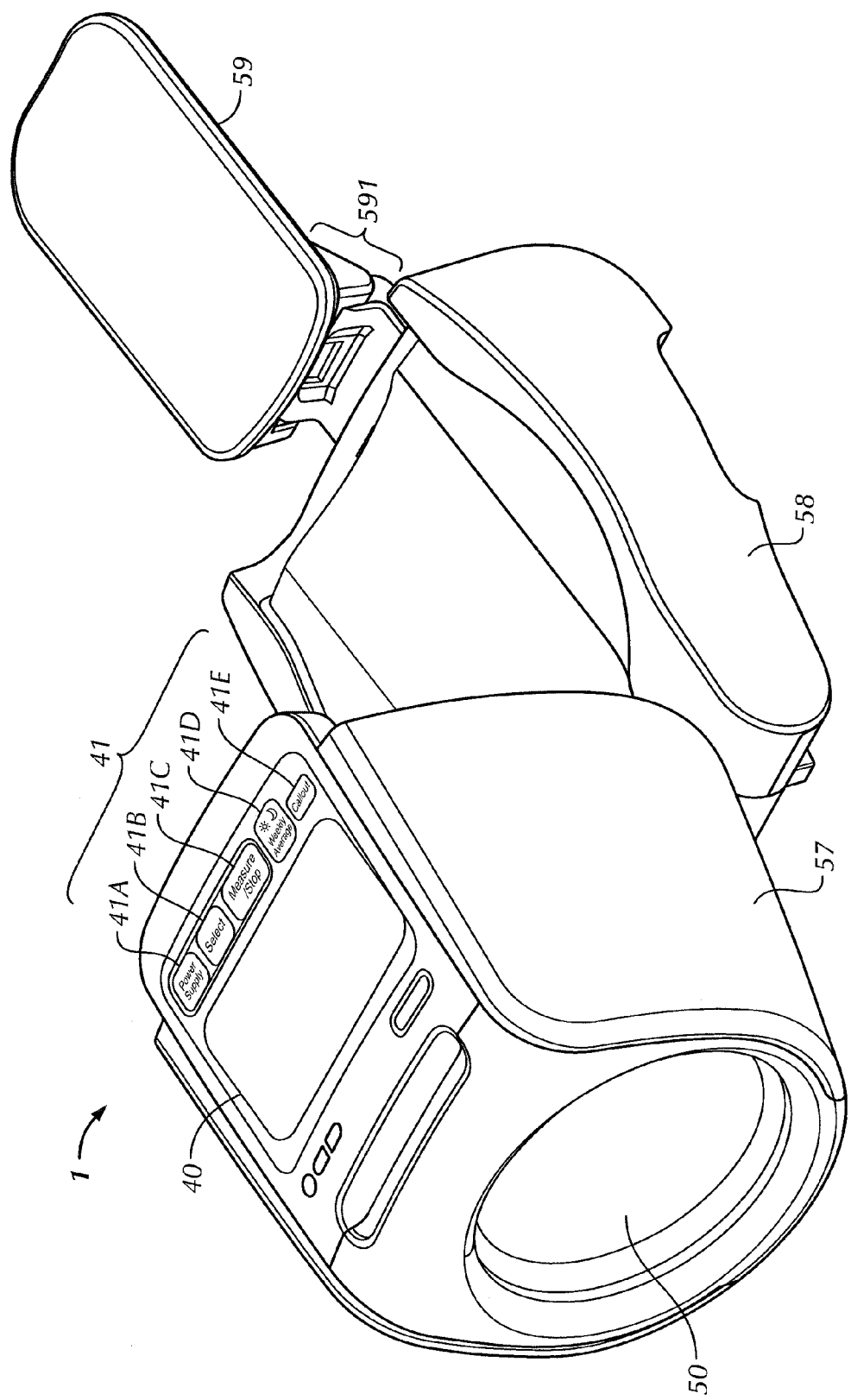
FIG. 1 is a schematic view of an automatic winding electronic sphygmomanometer according to one or more embodiments of the present invention.

Embodiments of the present invention will be hereinafter described in detail with reference to the drawings. In each figure, the same reference numerals indicate the same or corresponding portions, and the description thereof will not be repeated.

(Automatic Winding Electronic Sphygmomanometer)

An automatic winding electronic sphygmomanometer 1 is illustrated as a blood pressure measurement device according to one or more embodiments of the present invention. With reference to FIG. 1 to FIG. 4, the automatic winding electronic sphygmomanometer 1 includes a blood pressure measurement air bladder 50, a compressing and fixing air bladder 51 for fixing the blood pressure measurement air bladder 50 at a measurement site, a blood pressure measurement air system 52 for supplying or discharging the air to the blood pressure measurement air bladder 50 through a tube 53, an amplifier 35 arranged in relation to the blood pressure measurement air system 52, a pump drive circuit 36, a valve drive circuit 37, and an A/D (Analog/Digital) converter 38. Furthermore, the automatic winding electronic sphygmomanometer 1 includes a compressing and fixing air system 54 for supplying or discharging air to the compressing and fixing air bladder 51 through a tube 55, an amplifier 45 arranged in relation to the compressing and fixing air system 54, a pump drive circuit 46, a valve drive circuit 47, and an A/D (Analog/Digital) converter 48. Furthermore, the automatic winding electronic sphygmomanometer 1 includes a CPU (Central Processing Unit) 30 for intensively controlling and monitoring each unit, a memory 39 for storing various types of information such as the measured blood pressure value, a display unit 40 for displaying the various types of information including the blood pressure measurement result, an operation unit 41 operated to input various types of instructions for measurement, a timer 49 and a hinge unit 106 incorporating a sensor 107 to be described later. The blood pressure measurement air bladder 50 corresponds to the cuff herein.

The blood pressure measurement air system 52 includes a pressure sensor 32 for detecting and outputting the pressure (hereinafter referred to as cuff pressure) in the blood pressure measurement air bladder 50, a pump 33 for supplying air to the blood pressure measurement air bladder 50, and a valve 34 that is opened and closed to discharge or enclose the air of the blood pressure measurement air bladder 50. The amplifier 35 amplifies an output signal of the pressure sensor 32 and provides the amplified signal to the A/D converter 38. The A/D converter 38 converts the provided analog signal to a digital signal, and outputs to the CPU 30. The pump drive circuit 36 controls the drive of the pump 33 based on the control signal provided from the CPU 30. The valve drive circuit 37 opens and closes the valve 34 based on the control signal provided from the CPU 30.

The compressing and fixing air system 54 includes a pressure sensor 42 for detecting and outputting the pressure in the compressing and fixing air bladder 51, a pump 43 for supplying air to the compressing and fixing air bladder 51, and a valve 44 that is opened and closed to discharge or enclose the air of the compressing and fixing air bladder 51. The amplifier 45 amplifies an output signal of the pressure sensor 42 and provides the amplified signal to the A/D converter 48. The A/D converter 48 converts the provided analog signal to a digital signal, and outputs to the CPU 30. The pump drive circuit 46 controls the drive of the pump 43 based on the control signal provided from the CPU 30. The valve drive circuit 47 opens and closes the valve 44 based on the control signal provided from the CPU 30.

Figure 3:
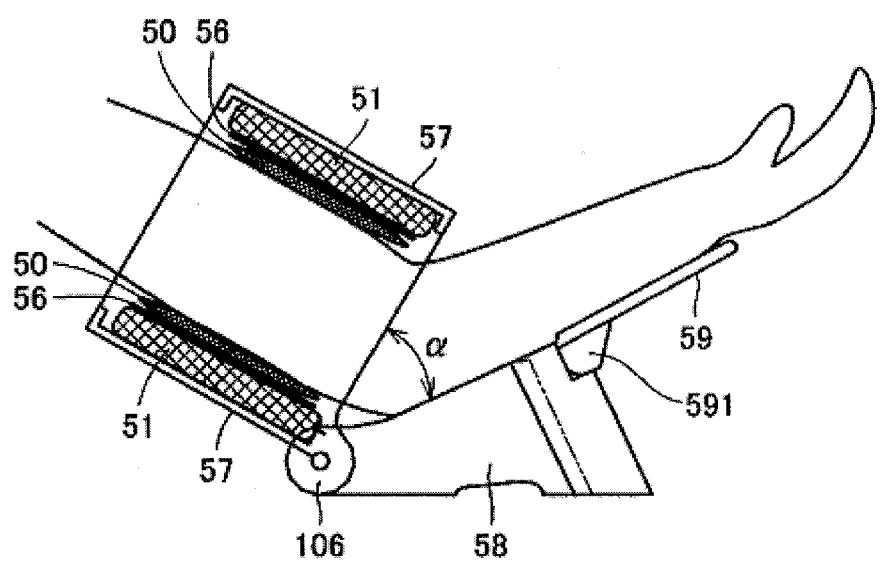
FIG. 3 is a view schematically showing a usage mode at the time of blood pressure measurement of the automatic winding electronic sphygmomanometer according to one or more embodiments of the present invention.
Figure 4:
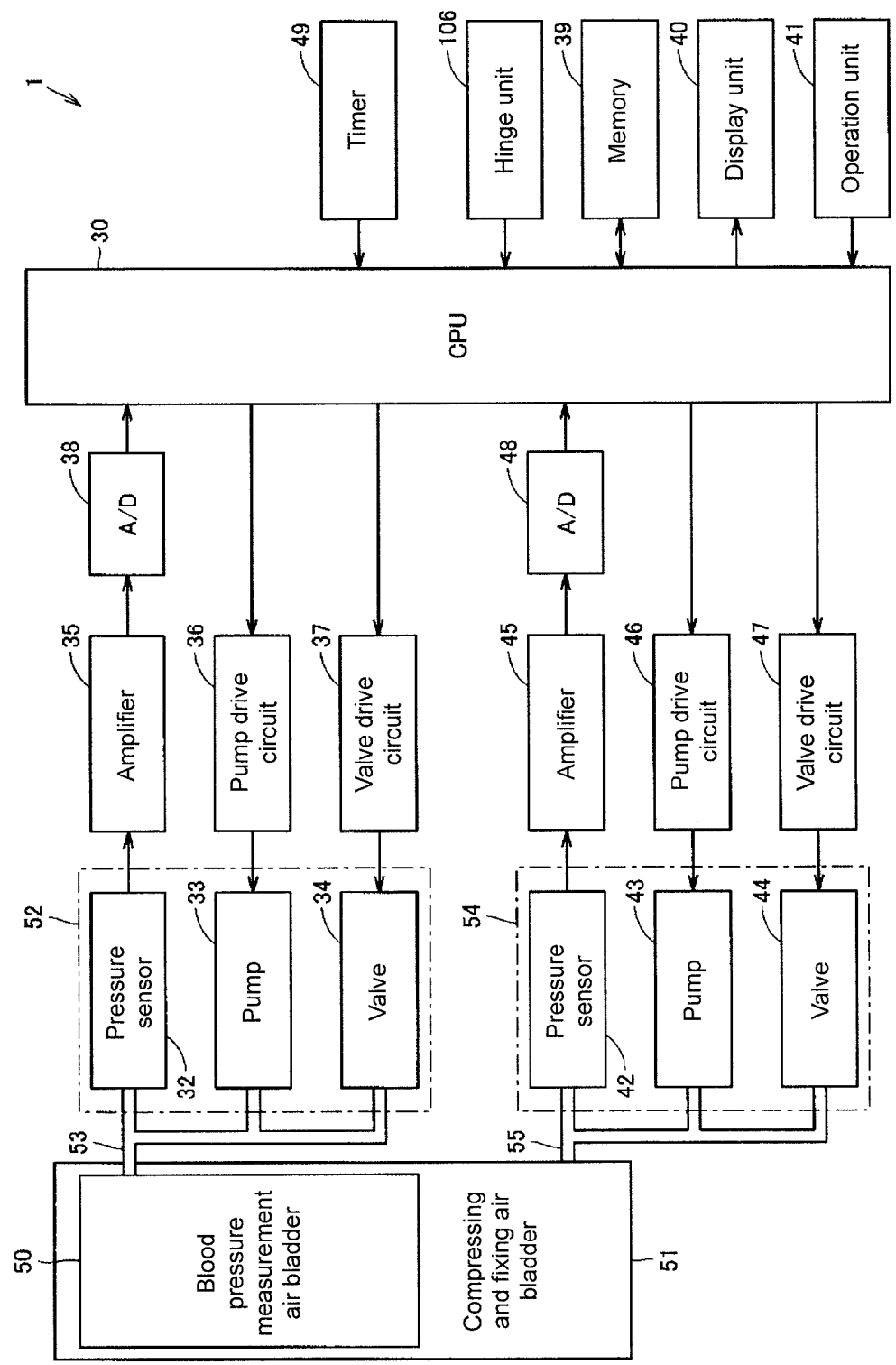
FIG. 4 is a hardware configuration of the automatic winding electronic sphygmomanometer according to one or more embodiments of the present invention.

With reference to FIG. 1 and FIG. 3, the automatic winding electronic sphygmomanometer 1 includes a fixing tubular case 57 for fixing the upper arm or the measurement site of the person to be measured, a sphygmomanometer main body 58, and a mounting portion 59 for placing the arm under the elbow joint at the time of the measurement. The fixing tubular case 57 includes the display unit 40 including an LCD (Liquid Crystal Display), and the operation unit 41 at an external position where an operation can be performed.

The operation unit 41 includes a power supply switch 41A, a switch 41B operated to select the person to be measured, a switch 41C for instructing start and stop of the blood pressure measurement, as well as a switch 41D and a switch 41E operated to read out the stored measurement data and display on the display unit 40 (callout display to be described later). The switch 41D is operated to call out and display a morning time zone measurement data and a night time zone measurement data to be described later.

According to one or more embodiments of the present invention, the automatic winding electronic sphygmomanometer 1 is assumed to be able to store the blood pressure measurement data for two people. The users A and B can be specified by the operation of the switch 41B. A visitor other than the users A and B can be specified with the operation of the switch 41B. If the visitor is specified, the blood pressure measurement can be carried out, but the blood pressure measurement data thereof is not stored.

The fixing tubular case 57 includes the blood pressure measurement air bladder 50 to be attached to the measurement site at the inner peripheral surface. FIG. 3 shows a state in which the upper arm or the measurement site of the person to be measured is inserted from the near side direction of the fixing tubular case 57 and fixed for the blood pressure measurement.

The automatic winding electronic sphygmomanometer 1 has the mounting portion 59 folded towards the sphygmomanometer main body 58 through a connecting portion 591 in time of no-use. The fixing tubular case 57 is collapsed towards the sphygmomanometer main body 58 through the hinge unit 106, so that they adopt an integrated configuration. At the time of the blood pressure measurement and when reading and displaying the stored measurement data, the person to be measured turns the fixing tubular case 57 in the near side direction (person to be measured side) in the figure through the hinge unit 106, as shown in FIG. 1, from the integrated configuration state to separate it from the sphygmomanometer main body 58. Thus, the person to be measured can insert the arm into the fixing tubular case 57, as shown in FIG. 3. In such a state, the fixing tubular case 57 and the sphygmomanometer main body 58 are connected through the hinge unit 106.

Figure 2:
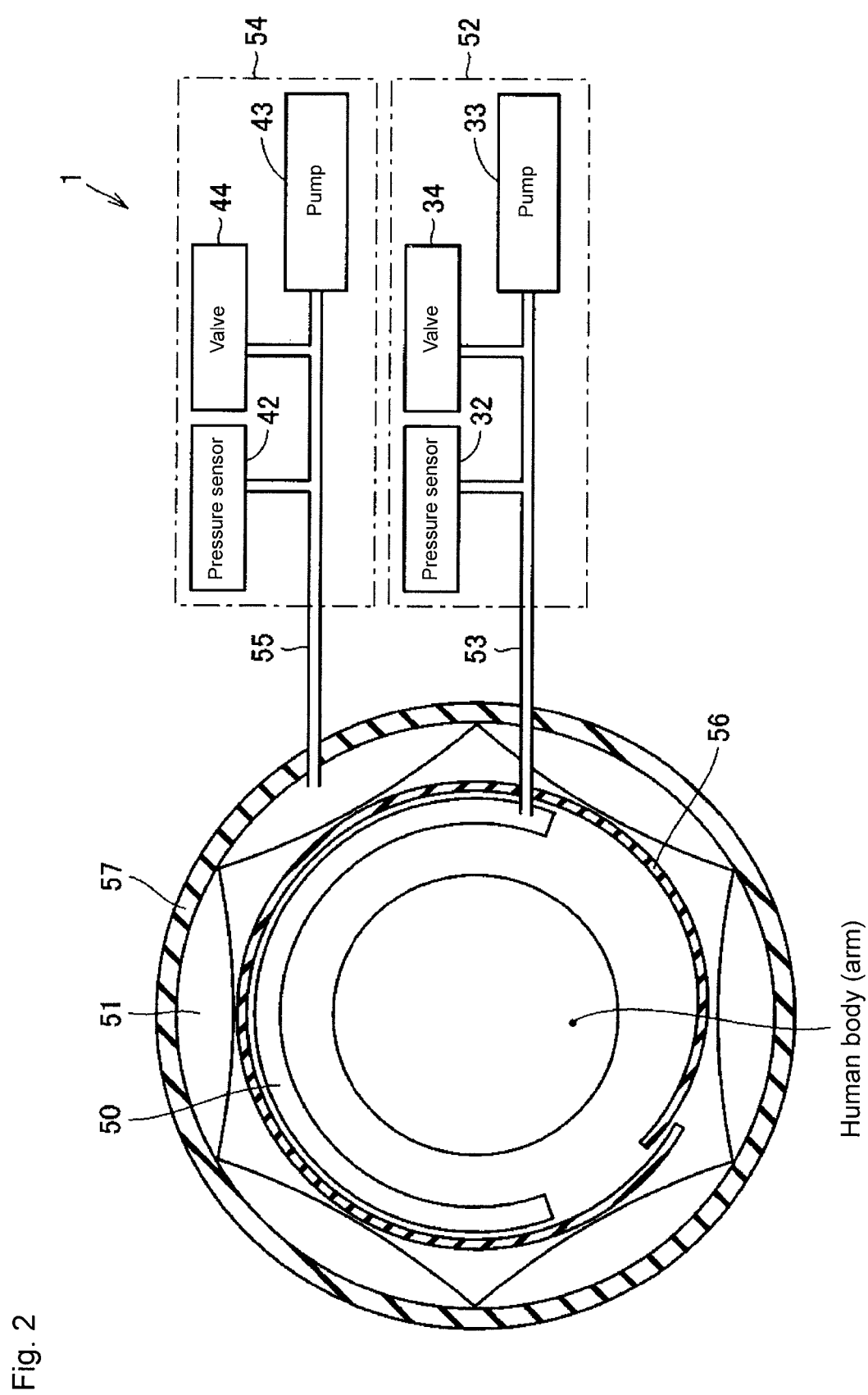
FIG. 2 is a schematic configuration diagram of an air system of the automatic winding electronic sphygmomanometer according to one or more embodiments of the present invention.

FIG. 2 schematically shows a transverse section of the fixing tubular case 57 in the state of FIG. 3. In the fixing tubular case 57, the blood pressure measurement air bladder 50, the compressing and fixing curler 56, and the compressing and fixing air bladder 51 are arranged so as to wrap around the periphery of the upper arm from the outer periphery of the upper arm or the measurement site towards the inner peripheral surface direction of the fixing tubular case 57. The compressing and fixing curler 56 is wrapped around the periphery of the upper arm. The shape of the compressing and fixing curler 56 becomes substantially circular along the periphery of the upper arm by winding. The diameter of substantially the circle is freely stretchable. When the air is gradually supplied by the compressing and fixing air system 54 to expand the compressing and fixing air bladder 51, the compressing and fixing curler 56 reduces the diameter by such action, and hence, the blood pressure measurement air bladder 50 interposed between the compressing and fixing curler 56 and the human body (upper arm) is pushed against the measurement site accompanied therewith. The blood pressure measurement air bladder 50 is wrapped around and fixed to the periphery of the human body (arm) by the compressing and fixing curler 56 and the compressing and fixing air bladder 51, so that the blood pressure measurable state can be realized.

(Regarding Function Configuration)

The function configuration of the automatic winding electronic sphygmomanometer 1 according to one or more embodiments of the present invention will be described with reference to FIG. 5. The automatic winding electronic sphygmomanometer 1 includes a pressure adjustment unit 101, a blood pressure calculating unit 102 including an average calculation portion 1021, an input determination unit 103, a display processing unit 104, and a tilt detection unit 105. The pressure adjustment unit 101 controls the pump drive circuits 36 and 46, as well as the valve drive circuits 37 and 47 to adjust the inner pressure of the blood pressure measurement air bladder 50 and the compressing and fixing air bladder 51.

The blood pressure calculating unit 102 calculates the blood pressure based on the signal input from the A/D converter 38, and stores the calculation result in the memory 39. The blood pressure calculating unit 102 also outputs the calculation result to the display processing unit 104 for display. The details of the functions of the blood pressure calculating unit 102 will be described later.

When detecting that time data indicates a predetermined day of the week (e.g., Sunday) every week based on the time data timed by the timer 49, the average calculation portion 1021 reads the blood pressure measurement data for one week from the memory 39, calculates the average measurement value based on the read measurement data for one week, and stores the calculated average data in the memory 39. The details of the functions of the average calculation portion 1021 will be described later.

The input determination unit 103 inputs the signal output when the operation unit 41 is operated by the person to be measured, determines which switch of the operation unit 41 is operated based on the input signal, and outputs the determination result. Specifically, the input determination unit 103 corresponds the signal level output when the switch is operated for every switch, and stores the same in advance. When the user operates the switch, the level of the signal input from the operation unit 41 and the stored level are compared and matched, and the type of switch to store is specified in correspondence with the matching level. Thus, the type of operated switch can be determined.

The tilt detection unit 105 is arranged in relation to the sensor 107 of the hinge unit 106. The sensor 107 detects the inclination angle (see angle α of FIG. 3) of the fixing tubular case 57 with respect to the sphygmomanometer main body 58 through the hinge unit 106. The signal of the detected inclination angle is provided to the tilt detection unit 105. The tilt detection unit 105 compares the angle indicated by the input tilt angle signal with a predetermined angle stored in advance, and outputs the signal based on the comparison result to the display processing unit 104 and the blood pressure calculating unit 102 as a tilt detection signal.

The display processing unit 104 has a function of displaying data on the display unit 40. Specifically, the display processing unit 104 includes a measurement processing portion 111 for carrying out the display of during the blood pressure measurement, a this-time measurement processing portion 112 for displaying the blood pressure measurement result for this time at the end of the blood pressure measurement, an each-time processing portion 113 for reading out and displaying the measurement result of each time stored in the memory 39, and an every-week processing portion 114 for reading out and displaying the average blood pressure measurement result in units of weeks stored in the memory 39.

The functions of the pressure adjustment unit 101, the blood pressure calculating unit 102, the input determination unit 103, the display processing unit 104, and the tilt detection unit 105 may be stored in the memory 39 as a program in advance, and the CPU 30 may read out such program from the memory 39 and execute the read program to realize the function of each corresponding unit.

Figure 5:
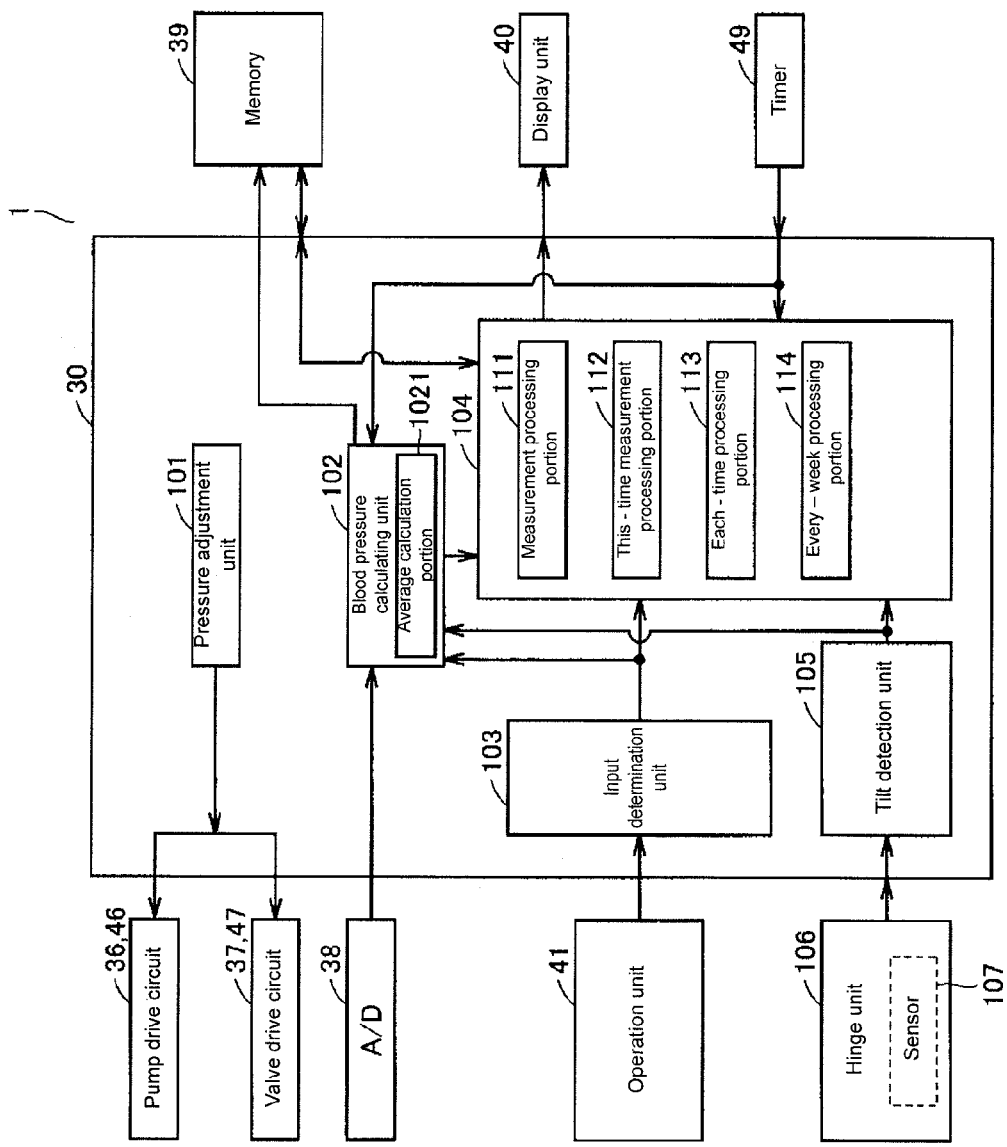
FIG. 5 is a function configuration diagram of the automatic winding electronic sphygmomanometer according to one or more embodiments of the present invention.

In FIG. 5, only the circuit related to the function executed by the CPU 30 is shown for the peripheral circuit to perform input and output with the CPU 30.

(Regarding Memory Configuration)

Figure 6:
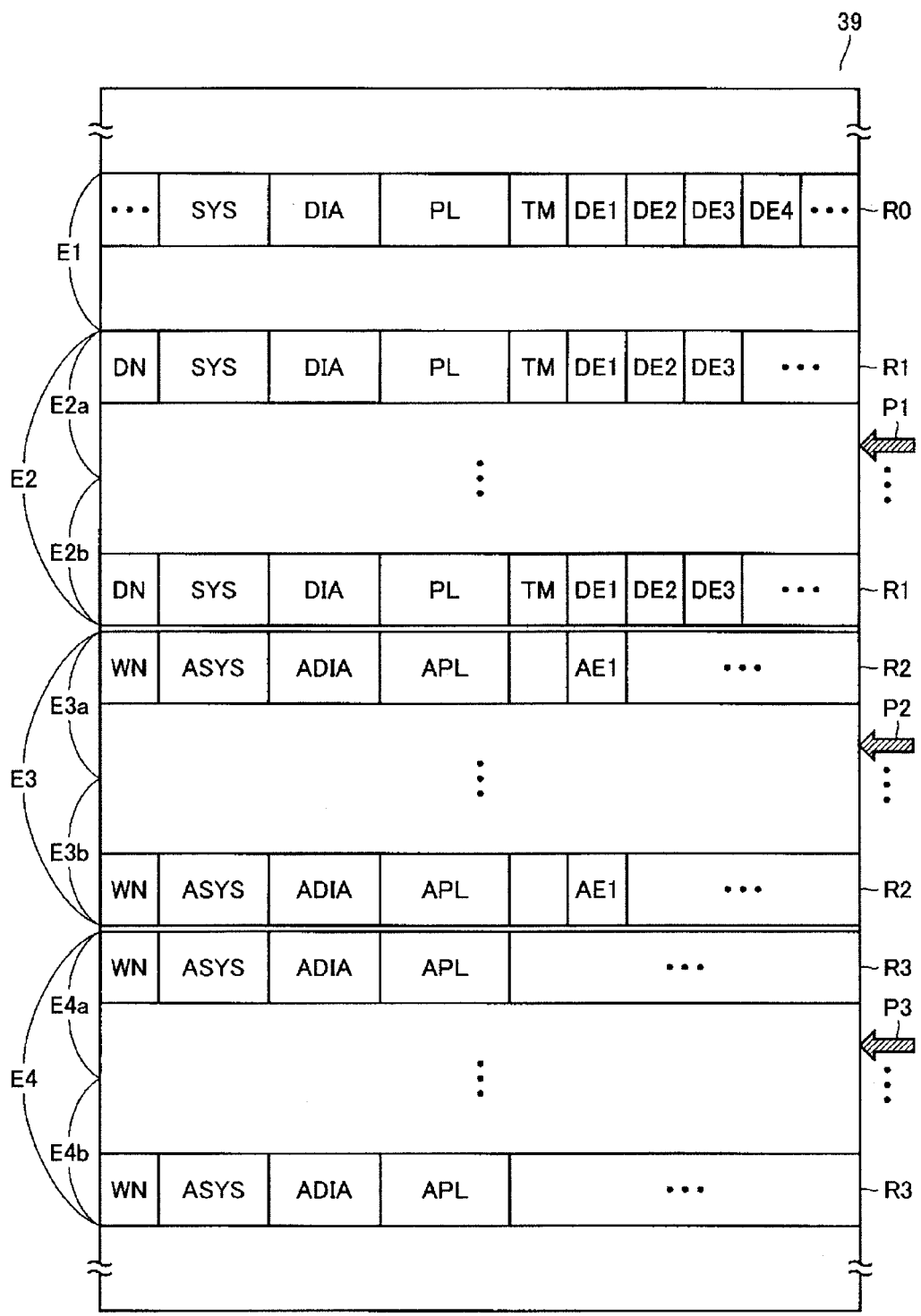
FIG. 6 is a memory configuration diagram of the automatic winding electronic sphygmomanometer according to one or more embodiments of the present invention.

FIG. 6 shows one example of a storage content of the memory 39. The memory 39 includes regions E1, E2, E3, and E4. The region E1 is a region where the measurement result is temporarily stored in the form of record R0 when the blood pressure measurement is performed. In each region E2, E3, and E4, a region for storing the blood pressure measurement result for the users A and B, respectively, or person to be measured is provided.

The record R0 of the region E1 or the blood pressure measurement result is read out every time the blood pressure measurement is carried out, and the read record R0 is stored in the form of record R1 in the region E2. More specifically, the record R1 of the blood pressure measurement result of the user A is stored in a region E2a of the region E2, and the record R1 of the blood pressure measurement result of the user B is stored in a region E2b of the region E2.

The average data of the morning time zone measurement data calculated for every week based on the blood pressure measurement result stored in the region E2 is stored in the form of record R2 in the region E3. More specifically, the average data of the morning time zone measurement data in units of weeks based on the data stored in the region E2a of the user A is stored in a region E3a. Similarly, the average data of the morning time zone measurement data in units of weeks based on the data stored in the region E2b of the user B is stored in a region E3b.

The average data of the night time zone measurement data calculated for every week based on the blood pressure measurement result stored in the region E2 is stored in the form of record R3 in the region E4. More specifically, the average data of the night time zone measurement data in units of weeks based on the data stored in the region E2a of the user A is stored in a region E4a. Similarly, the average data of the night time zone measurement data in units of weeks based on the data stored in the region E2b of the user B is stored in a region E4b.

The record R0 of the region E1 includes, for the blood pressure measurement result for this time, systolic blood pressure data SYS, diastolic blood pressure data DIA, pulse rate data PL, measurement time data TM, data DE1 indicating whether or not corresponding to the early morning high blood pressure, data DE2 indicating whether or not the person to be measured moved the body during the blood pressure measurement, data DE3 indicating whether or not the tilt angle of the fixing tubular case 57 is shifted from a predetermined angle for normal measurement, that is, tilted, and data DE4 for identifying the user.

The data TM indicates the measurement time. The blood pressure calculating unit 102 stores the time data input from the timer 49 in the record R0 as the data TM.

The data DE4 indicates distinguishing of the person to be measured instructed by the operation of the switch 41B. The signal input from the input determination unit 103 by the blood pressure calculating unit 102 is stored in the record R0 as the data DE4.

The data DE3 indicates the detection result on whether or not the angle $\alpha$ of the fixing tubular case 57 the tilt detection unit 105 detects by the sensor 107 during the blood pressure measurement is deviated from the range of a predetermined angle. The range of the predetermined angle is the range of the angle $\alpha$ detected when the measurer is in the normal measurement position. The data of the range of the predetermined angle is assumed to be detected through experiment or the like in advance, and stored in a predetermined storage region of the memory 39.

The data DE2 indicates the result of detecting whether or not the person to be measured moved the body during the blood pressure measurement. If the person to be measured moved the body during the measurement, the measurement accuracy is known to become low. The CPU 30 can detect the presence or absence of the body motion based on the waveform of the pulse wave detected during the blood pressure measurement. The well known technique can be applied for the detection procedure of the body motion, and hence, the details thereof will be omitted. The determination result of the angle of the fixing tubular case 57 by the tilt detection unit 105 and the detection result of the presence or absence of the body motion are output to the blood pressure calculating unit 102. The blood pressure calculating unit 102 stores the detection result input from the tilt detection unit 105 and the detection result of the body motion in the record R0 as the data DE2 and the DE3, respectively.

The record R1 stored in the region E2a includes the data DN indicating the serial number complying with the order stored in the region E2a, that is, the order of the measurement time, the data SYS, DIA, PL, and TM, as well as the data DE1, DE2, and DE3. The record R1 is similarly stored in the region E2b for the user B. A maximum of 99 records R1 can be stored in each region E2a and E2b.

The record R2 of the region E3a includes the data showing the average of the measurement data in units of one week calculated based on the record R1 in which the data TM indicates the morning time zone of the record R1 stored in the region E2a. The record R2 includes the data WN indicating which week's data, the data ASYS indicating the average of the systolic blood pressure data SYS of the morning time zone measurement for one week, the data ADIA indicating the average of the diastolic blood pressure data DIA of the morning time zone measurement for one week, the data APL indicating the average of the pulse rate data PL of the morning time zone measurement for one week, and the data AE1 indicating whether or not the average blood pressure indicated by the data ASYS and ADIA stored in the record R2 indicates early morning high blood pressure. Similarly, the record R2 of the region E3b includes the data ASYS, ADIA, APL, and AE1 calculated in units of one week based on the data stored in the region E2b.

The record R3 of the region E4a includes the data ASYS, ADIA, and APL of the average value in units of one week of the night time zone measurement data based on the record R1 in which the data TM indicates the night time zone of the record R1 stored in the region E2*a*. Similarly, the record R3 of the region E4*b* includes the data ASYS, ADIA, and APL of the average value in units of one week of the night time zone measurement data based on the record R1 in which the data TM indicates the night time zone of the record R1 stored in the region E2*b*.

The records for a maximum of seven weeks are stored in each region E3*a*, E3*b*, E4*a*, and E4*b*. Specifically, the records for a total of seven weeks, this week (data WN indicates '0'), last week (one week before: data WN indicates '1'), week before last (two weeks before: data WN indicates '2'), . . . six weeks before (six weeks before; data WN indicates '3'). If the data for this week is newly calculated, the newly calculated content is overwritten on the record stored in the past the most, that is, the record in which the value indicated by the data WN is '6'. When such overwrite is carried out, the value of the data WN of the record is updated '6'→'0', and the values of the data WN of other records are updated by +1.

A pointer P1, P2, and P3 is arranged in each region E2, E3, and E4, respectively. The pointer P1 points to the record R1 in which the data is currently read in the region E2. The pointer P2 points to the record R2 in which the data is currently read in the region E3. The pointer P3 points to the record R3 the data is currently read in the region E4.

(Regarding Blood Pressure Calculation/Average Calculation Function)

The blood pressure calculating unit 102 calculates the blood pressure (maximum blood pressure (systolic blood pressure) and minimum blood pressure (diastolic blood pressure)) according to a well-known method such as the oscillometric method based on the pulse wave signal input from the A/D converter 38. The pulse is also calculated by a well-known method.

Furthermore, the blood pressure calculating unit 102 determines whether or not corresponding to the early morning high blood pressure, the presence or absence of the body motion during the measurement, whether or not the tilt angle α of the fixing tubular case 57 during the measurement is appropriate, and the user each time the blood pressure measurement is performed, and stores the determination result in the memory 39 in association with the measurement data.

According to The Japanese Society of Hypertension, it is defined as high blood pressure if the systolic blood pressure is higher than or equal to 135 mmHg or the diastolic blood pressure is higher than or equal to 85 mmHg in home blood pressure. In particular, if the blood pressure after waking up corresponds to the category of the high blood pressure, it is defined as the early morning high blood pressure. The early morning high blood pressure becomes the factor that increases the cardiovascular risk. Therefore, according to one or more embodiments of the present invention, if detected that the blood pressure measurement is carried out from 4 AM to 10 AM in one day based on the timing data of the timer 49, it is determined as the morning time zone measurement, and if detected that the measurement is carried out from 7 p.m. to 2 a.m., it is determined as the night time zone measurement. Furthermore, the morning time zone measurement data SYS and DIA, and the index data (135 mmHg/85 mmHg) of the high blood pressure are compared, and whether or not the early morning high blood pressure is detected based on the comparison result. The detection result is stored as the data DE1.

The data indicating the morning/night time zone (4 a.m. to 10 a.m./7 p.m. to 2 a.m.) and the index data (135 mmHg/85 mmHg) of the high blood pressure are stored in a predetermined storage region of the memory 39 in advance.

The average calculation portion 1021 inputs the signal by the operation of the switch 41B through the input determination unit 103, and identifies the user based on the input signal. The past measurement data stored in the region of the memory 39 corresponding to the identified user is searched, and the morning time zone measurement data for one week are read out. The average data of the read data is calculated. Similarly, the average data of the night time zone measurement data for one week is calculated.

Specifically, if determined that the timing data of the timer 49 indicates a predetermined day of the week (e.g., Sunday), the measurement data of the record R1 of the morning time zone for one week in the past (measurement data of the record R1 in which the data TM indicates 4 a.m. to 10 a.m.) is read out from the region E2 of the memory 39 for every user, the average of the read measurement data for one week is calculated, and the calculated result is stored in the region E3 of the memory 39. Similarly, the measurement data of the night time zone for one week in the past (measurement data of the record R1 in which the data TM indicates 7 p.m. to 2 a.m.) is read out from the region E2 of the memory 39 for every user, the average of the read measurement data for one week is calculated, and the calculated result is stored in the region E4 of the memory 39.

The average calculation portion 1021 compares the calculated morning time zone average measurement data ASYS and ADIA and the index data (135 mmHg/85 mmHg) of the high blood pressure, and detects whether or not the data corresponds to the category of the early morning high blood pressure based on the comparison result. The detection result is stored in the record R2 as the data AE1.

The average calculation portion 1021 calculates the average of the measurement data of the morning time zone and the night time zone for this week based on the measurement data of the record R1 of the morning time zone and the night time zone for this week (Sunday immediately before to today) of the region E2 for every user every time the blood pressure measurement is carried out every day, and stores the result in the regions E3 and E4, respectively, of the memory 39 as the records R2 and R3 (data WN is '0').

(Blood Pressure Measurement Process)

Figure 7:
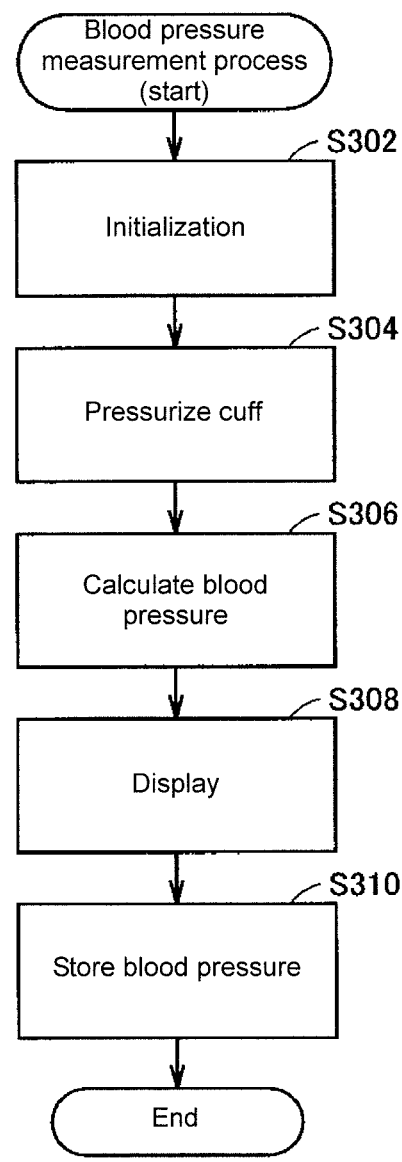
FIG. 7 is a flowchart of a blood pressure measurement process according to one or more embodiments of the present invention.

The blood pressure measurement process according to one or more embodiments of the present invention will be described according to the flowchart of FIG. 7. The program according to the flowchart of FIG. 7 is stored in a predetermined storage region of the memory 39, where the blood pressure measurement process is realized when the CPU 30 reads out the program and executes the read program.

The blood pressure measurement process shown below is an example and is not particularly limited thereto.

In the measurement state shown in FIG. 3, the CPU 30 first performs the initialization process (step S302). Specifically, the exhaust of air of the blood pressure measurement air bladder 50 and the compressing and fixing air bladder 51, the correction of the pressure sensors 52 and 54, and the like are performed.

When the measureable state is achieved, the pressure adjustment unit 101 adjusts the pump drive circuits 36 and 46 according to a predetermined procedure, and gradually increases the pressure of the blood pressure measurement air bladder 50 and the compressing and fixing air bladder 51 (step S304). When the blood pressure measurement air bladder 50 is wrapped around and fixed to the measurement site by the compressing and fixing air bladder 51, the inner pressure (cuff pressure) of the blood pressure measurement air bladder 50 is gradually increased, and the inner pressure is detected as indicating a predetermined level for the blood pressure measurement, the pressure adjustment unit 101 controls the pump drive circuit 36 to stop the pump 33. According to one or more embodiments of the present invention, the blood pressure calculation is carried out in the pressurization process from the start of the pressurization until the detection that the inner pressure indicates a predetermined level.

In the pressurization process, the blood pressure calculating unit 102 calculates the blood pressure (systolic blood pressure, diastolic blood pressure) through a known procedure based on the pressure pulse wave signal detected through the A/D converter 38 (step S306). The blood pressure calculating unit 102 also calculates the pulse rate through a known procedure.

The calculated blood pressure and pulse rate are stored in the region E1 of the memory 39 as the record R0, and the content of the record R0 is provided to this-time measurement processing portion 112 of the display processing unit 104. The this-time measurement processing portion 112 generates image data based on the provided data and outputs the same to the display unit 40 (step S308). Therefore, the display unit 40 displays a screen based on the input image data.

Following the display process of step S308, the blood pressure calculating unit 102 generates the record R1 based on the data of the record R0, and stores the generated record R1 in the region of the relevant user in the region E2 of the memory 39 (step S310). The person to be measured is assumed to be selected in advance by the operation of the switch 41B as user A or B, and hence, the generated record R1 is stored in the region E2a or E2b.

After the blood pressure measurement, the air of the blood pressure measurement air bladder 50 and the compressing and fixing air bladder 51 is rapidly exhausted, and the measurement process is terminated.

The display process of step S308 may be carried out after the storage process of step S310. The blood pressure measurement is performed in the pressurization process, but may be performed in the depressurization process.

As hereinafter described, a bar graph shaped indicator displaying the blood pressure value may be displayed in the screen of the display unit 40. The measurement processing portion 111 may display the blood pressure value sequentially detected by the pressure sensor 32 and the A/D converter 38 with an increase in the cuff pressure in the pressurization process (step S304) on the screen by bar graph and digital number.

(Callout and Display Process)

According to one or more embodiments of the present invention, the blood pressure measurement data stored in the memory 39 is read out and the read blood pressure measurement data is displayed on the display unit 40 in response to the instruction by the operation of the operation unit 41. This is called the callout and display process. According to one or more embodiments of the present invention, the switch 41D or the switch 41E is operated to instruct the callout and display process.

Assume here that the sufficient number of records R1, R2, and R3 are stored in the memory 39 in ascending order of values of the data DN and WN. Assume also that the user is specified by the operation of the switch 41B. Therefore, a case where the callout and display process is performed on the blood pressure measurement data of the user A will be described. The process is similarly performed even when the switch 41B is operated and the user B is specified.

First, the callout and display process of when the switch 41E is operated will be described.

When the switch 41E is operated, the data of the record R1 pointed out by the pointer P1 is read from the region E2 by the each-time processing portion 113 for every user specified by the switch 41B, the image data for display is generated based on the read data, and the generated image data is provided to the display unit 40. Therefore, a screen based on the measurement data of the record R1 pointed out by the pointer P1 that moves every time the switch 41E is operated is switched and displayed on the display unit 40.

Figure 8:
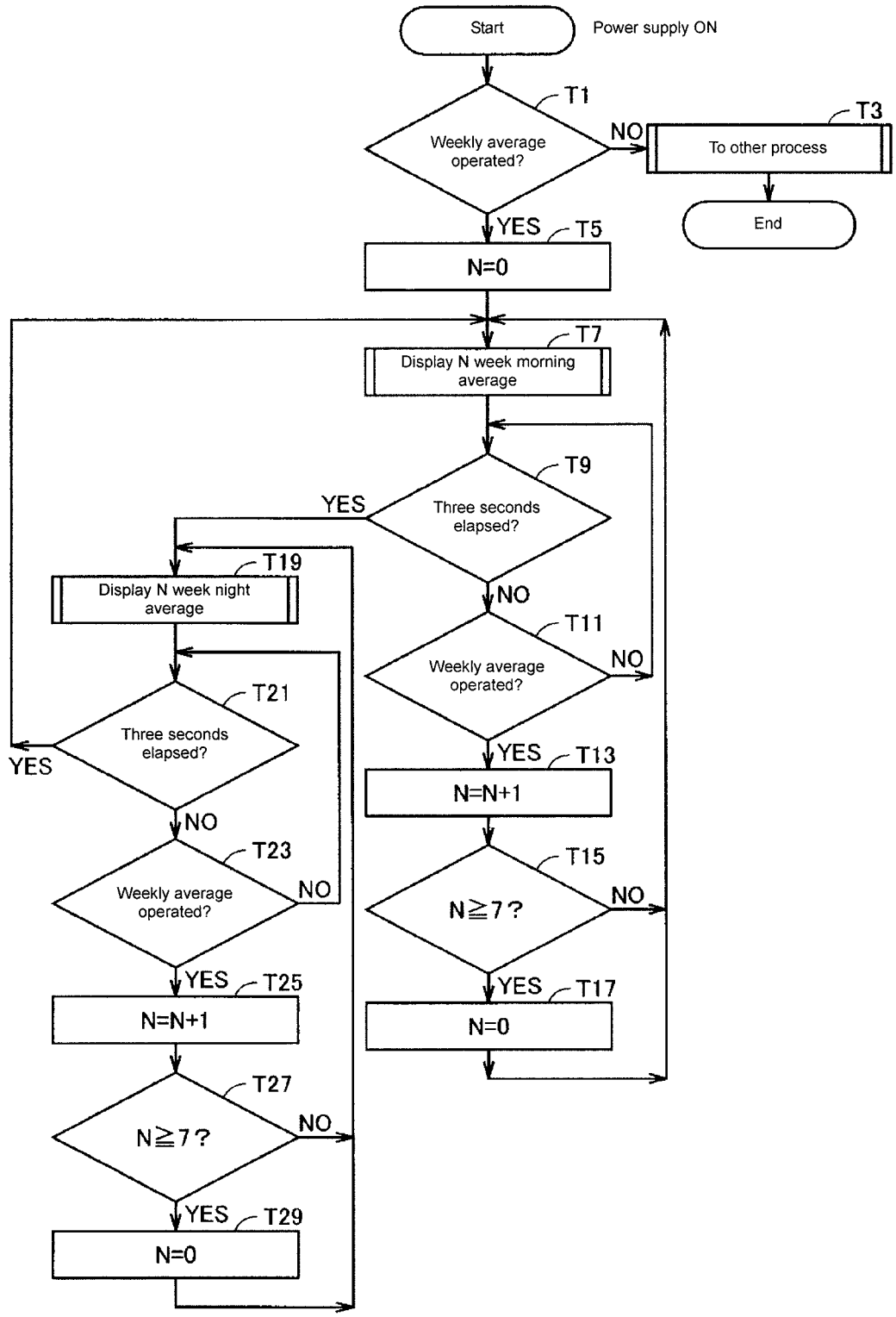
FIG. 8 is a flowchart showing one example of a callout and display process according to one or more embodiments of the present invention.

The callout and display process by the every-week processing portion 114 of when the switch 41D is operated will now be described according to the flowchart of FIG. 8. The program according to the flowchart of FIG. 8 is stored in a predetermined storage region of the memory 39, where the following process is realized when the CPU 30 reads out the program and executes the read program.

Assume that the switch 41A is operated and the power is supplied to each unit of the automatic winding electronic sphygmomanometer 1 (power supply ON). The input determination unit 103 of the CPU 30 determines the type of operated switch of the operation unit 41 based on the output signal from the operation unit 41 (step T1). When the input determination unit 103 determines that the switch 41D is operated based on the determination result (YES in step T1), the process proceeds to step T5 to be described later. When not determined that the switch 41D is operated (NO in step T1), other processes (step T3) complying with the operated switch are performed.

In step T5, a value 0 is set to a temporary variable N indicating the value of the pointer of the memory 39. The pointers P2 and P3 of the memory 39 thus respectively point to the records R2 and R3 stored at the head of the respective region E3a and E4a.

On the basis of the determination result on the type of operated switch by the input determination unit 103, the every-week processing portion 114 of the display processing unit 104 then reads out the data of the record R2 of the region E3a pointed out by the pointer P2, generates data of the image to be displayed based on the read data, and provides the generated data to the display unit 40. Therefore, the image based on the image data is displayed on the display unit 40 (step T7). One example of the display image in step T7 is shown in FIG. 9 and FIGS. 10A to 10D to be described later.

The CPU 30 then determines whether or not a time of three seconds has elapsed (step T9) without the switch 41D being operated (NO in step T11) from the start of displaying of the image in step T7 based on the time data output by the timer 49.

Figure 11:
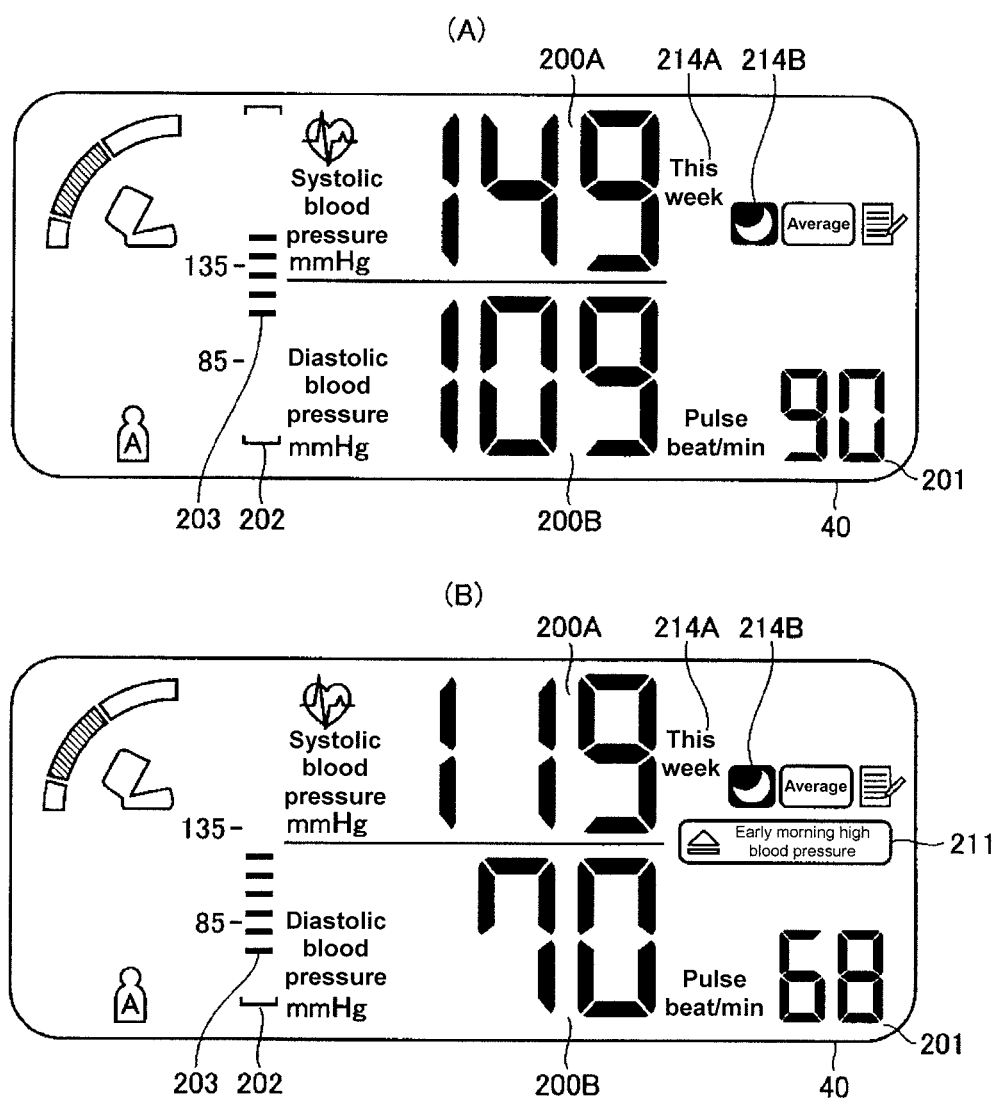
FIGS. 11A and 11B are views showing another further example of the display according to one or more embodiments of the present invention.

If determined that three seconds have elapsed without the switch 41D being operated (NO in step T11, YES in step T9), the CPU 30 instructs the every-week processing portion 114 to display the image based on the record R3 pointed out by the pointer P3. In response to such instruction, the every-week processing portion 114 reads out the data of the record R3 pointed out by the pointer P3 of the region E4a of the memory 39, generates the data of the image to be displayed based on the read data, and provides the generated data to the display unit 40. Therefore, the image based on the image data generated by the data of the record R3 is displayed on the display unit 40 (step T19). The image of the display unit 40 thus switches from the image of step T7 to the image of step T19. One example of the image displayed in step T19 is shown in FIGS. 11A and 11B.

The CPU 30 then determines whether or not a time of three seconds has elapsed (step T21) without the switch 41D being operated (NO in step T23) from the start of displaying of the image in step T19 based on the time data output by the timer 49.

If determined that three seconds have elapsed without the switch 41D being operated (NO in step T23, YES in step T21), the process returns to step T7, and the processes after step T7 are performed similar to the above. Therefore, the image is switched to the image of step T7, which was displayed before the image is displayed in step T19, for display on the display unit 40.

Thus, the operation of alternately switching and displaying the average data of the morning time zone and the average data of the night time zone for this week or N weeks before indicated by the value of the variable N at a three-second interval on the screen of the display unit 40 is continued by simply operating the switch 41D once.

If the person to be measured operates the switch 41D before the elapse of three seconds from the start of display of the average data of the morning time zone for this week or N weeks before (NO in steps T7, T9, YES in step T11), the value of the variable N is updated +1. The pointers P2 and P3 thus point to the records R2 and R3 of the week of the next order (step T13). As a result, if determined that (N≥7) is not met, that is, if determined that the record pointed out by the pointer indicates one of the records of this week, last week, week before last, three weeks before, . . . five weeks before (NO in step T15), the process returns to step T7. In the processes after step T7, the callout and display process of the average data of the morning time zone of the record R2 pointed out by the current pointer P2 is performed similar to the above.

If the switch 41D is pushed within three seconds after the start of display of the average data of the morning time zone of a maximum week before (six weeks before) (step T7, NO in T9, YES in step T11, step T13, YES in step T15), the value of the variable N is set to 0 (step T17). The pointer P2 thus points to the record R2 (average data of this week) stored at the head of the region E2a as the data to be called out and displayed. Thereafter, the process returns to step T7, and the subsequent processes are similarly performed.

As a result, after the average data of a maximum week before (six weeks before) is displayed, the average data of the morning time zone of this week is called out and displayed, and subsequently, the callout and display process of the average data of the morning time zone of last week, week before last, three weeks before . . . can be carried out.

The process similar to the callout and display process of the average data of the morning time zone described above is carried out by the update of the value of the pointer P3 with respect to the average data of the night time zone of the region E3a (step T19, NO in T21, YES in step T23, step T25, YES in step T27, step T29). The average data of the night time zone of this week is called out and displayed after the display of the average data of the night time zone of a maximum week before (six weeks before).

Therefore, if the person to be measured operates the switch 41D before an elapse of three seconds after the start of the display of the average data of the morning time zone (or night time zone) of this week (N=0) or N (N=1, 2, . . . , 5) weeks before, the callout and display process of the average data of the morning time zone (or night time zone) of (N+1) week before or the measurement time of the next order is performed.

Figure 9:
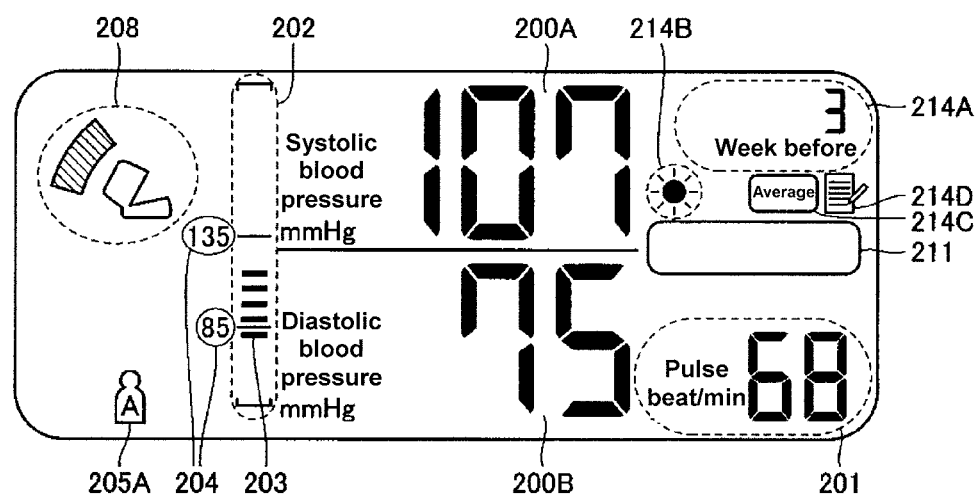
FIG. 9 is a view showing one example of a display according to one or more embodiments of the present invention.

One example of the display screen of step T7 is shown in FIG. 9. With reference to FIG. 9, in the screen of the display unit 40, the data 200A and 200B corresponding to the data ASYS and ADIA of the record R2 of the pointer P2, the pulse rate data 201 corresponding to the data APL, the blood pressure level bar 202 for displaying the blood pressure value of the data 200A and 200B with a rectangular bar graph, the data 205A indicating another user, the data 208 indicating the tilt of the fixing tubular case 57 based on the detection signal by the tilt detection unit 105, and the data 214A indicating how many weeks before based on the data WN are simultaneously displayed on the same screen. The data 214B of a sun mark indicating that it is the measurement data of the morning time zone, the data 214C indicating that the display data is average data, and the data 214D indicating that the display data is past measurement data read from the memory 39 are also simultaneously displayed. The sun mark of the data 214B matches the mark (see FIG. 1) given to the switch 41D operated to display the relevant measurement data. It is not limited to the sun mark to indicate the morning time zone, and other marks, characters ("morning") or the like may be used.

The average data of the morning time zone is displayed herein, but a moon mark is displayed for the data 214B when displaying the average data of the night time zone. This mark matches the mark (see FIG. 1) given to the switch 41D operated to display the relevant measurement data. It is not limited to the moon mark to indicate the night time zone, and other marks, characters ("night") or the like may be used.

In the screen of the display unit 40, the data 211 indicating whether or not it corresponds to the early morning high blood pressure based on the data AE1 of the record R2 may be displayed. The screen of FIG. 9 shows a case where the data AE1 of the record R2 that is called out and displayed does not indicate the early morning high blood pressure.

In FIG. 9, the criterion value 204 for sectionalizing the early morning high blood pressure is displayed in association at the position indicating the blood pressure value corresponding to the criterion value 204 on the blood pressure level bar 202. The criterion value 204 is displayed herein, but it may be printed in advance on the screen of the display unit 40.

Furthermore, in FIG. 9, a bar graph in which a plurality of marks 203 is continued is displayed to show the value of the blood pressure indicated by the data 200A and 200B while being superimposed on the blood pressure level bar 202. The rectangular mark 203 as a scale for sectionalizing into segments of units of 10 mmHg is displayed on the blood pressure level bar 202 so that the user can easily read the value of the bar graph.

In the figure of the other screen display example, the description of the reference numerals to the same portion or the corresponding portion as FIG. 9 is omitted for clarification.

Figure 10:
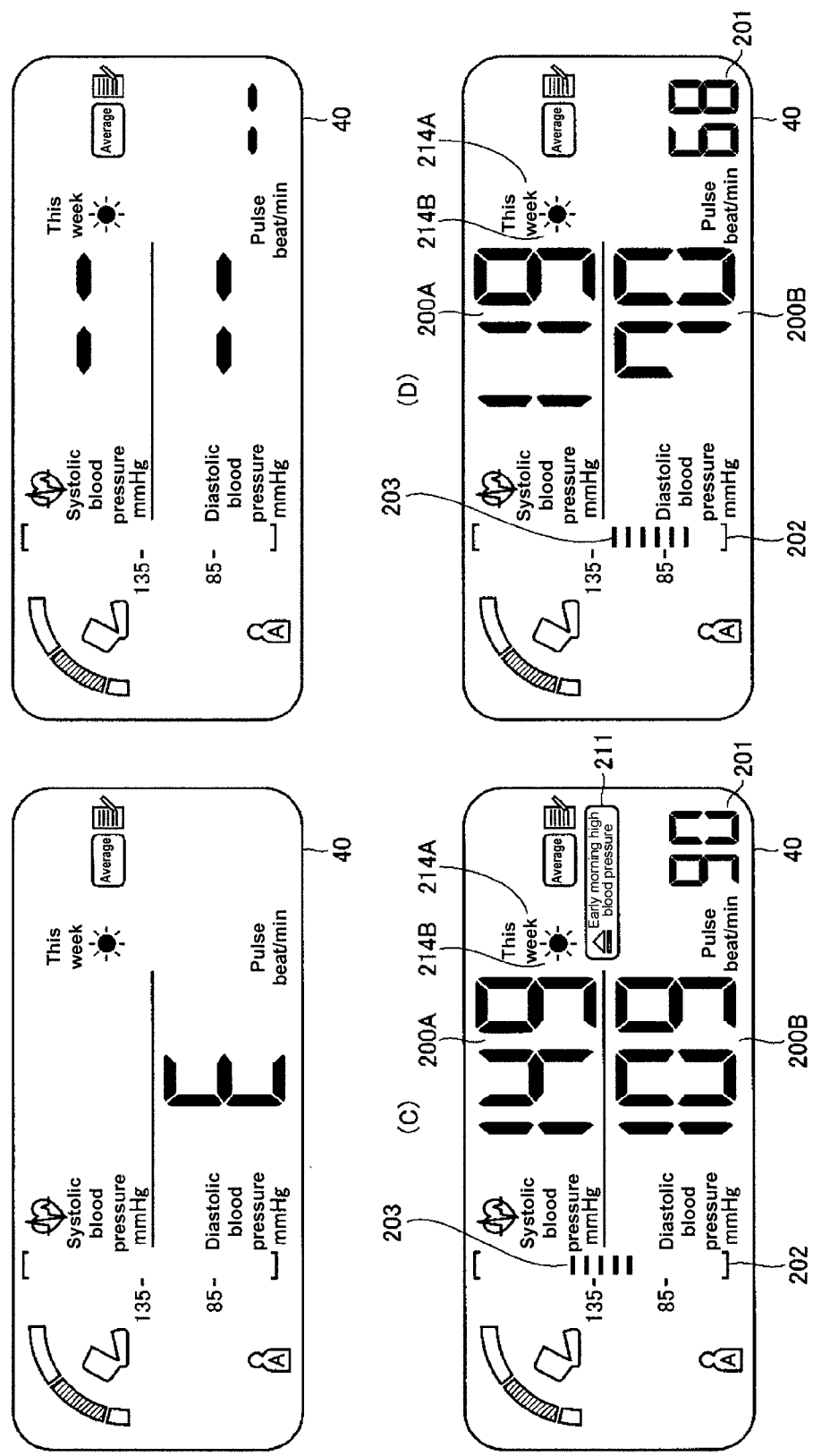
FIGS. 10A to 10D are views showing another example of the display according to one or more embodiments of the present invention.

In FIGS. 10A to 10D, the screen display of the callout and the display of the average data for this week in step T7 is shown. FIGS. 10A and 10B are display examples of when the data reading from the memory 39 is not normally performed. In FIG. 10A, the error in data reading is indicated with the character representation of "E". FIG. 10B is a display example of when the average data to be read is not stored in the memory 39.

FIGS. 10C and 10D are screen examples of the callout and display of the average data of the morning time zone of this week. In FIG. 10C, it is notified that the average data of the morning time zone of this week corresponds to the category of "early morning high blood pressure" by the data 211.

FIGS. 11A and 11B are screen examples of the callout and display of the average data of the night time zone of this week according to the record R3 pointed by the pointer P3 in step T19. In FIG. 11B, it is notified that the average data of the morning time zone of this week corresponds to the category of "early morning high blood pressure" by the data 211, and notification is made that the average data does not correspond in FIG. 11A. The data 211 is displayed based on the data AE1 in the record R2 pointed out by the pointer P2 when displaying the screen of FIG. 11B. Therefore, the average data of the night time zone of a certain week and the information indicating that the average data of the morning time zone of the corresponding week corresponds to the category of the early morning high blood pressure can be simultaneously checked on the same screen.

Figure 12:
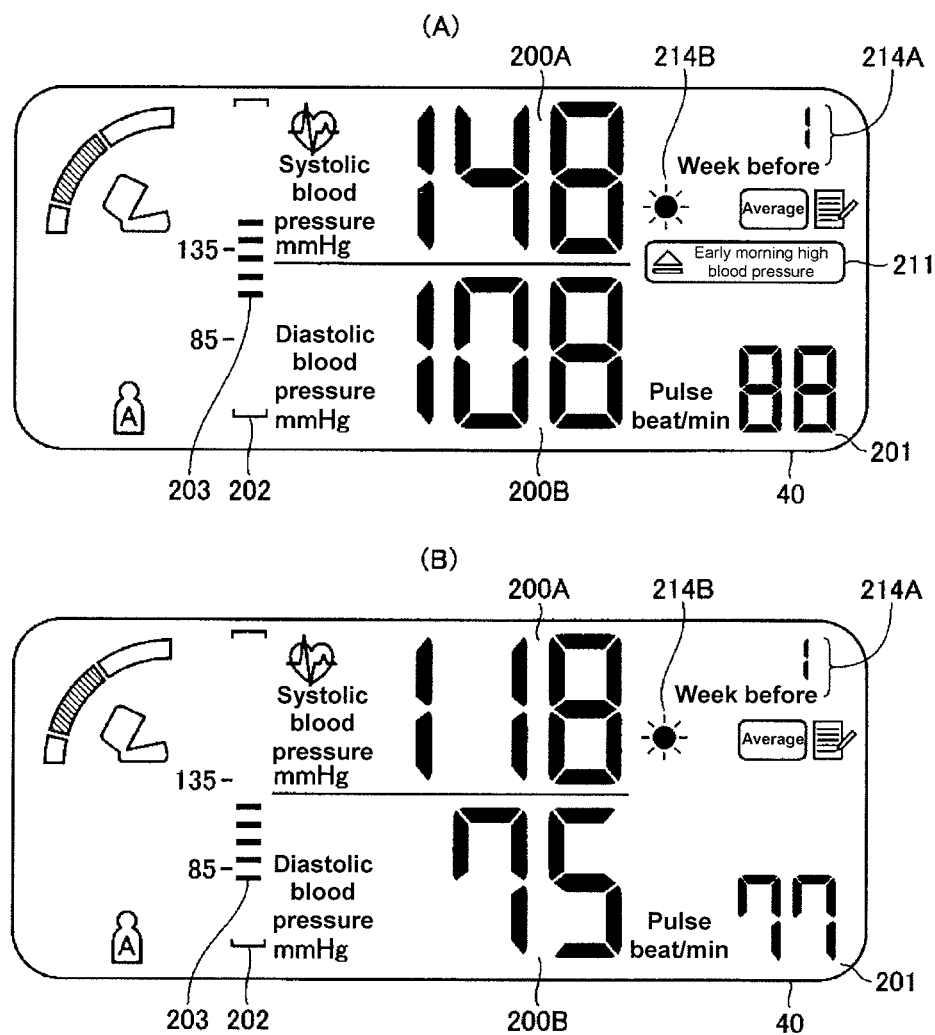
FIGS. 12A and 12B are views showing another further example of the display according to one or more embodiments of the present invention.
Figure 13:
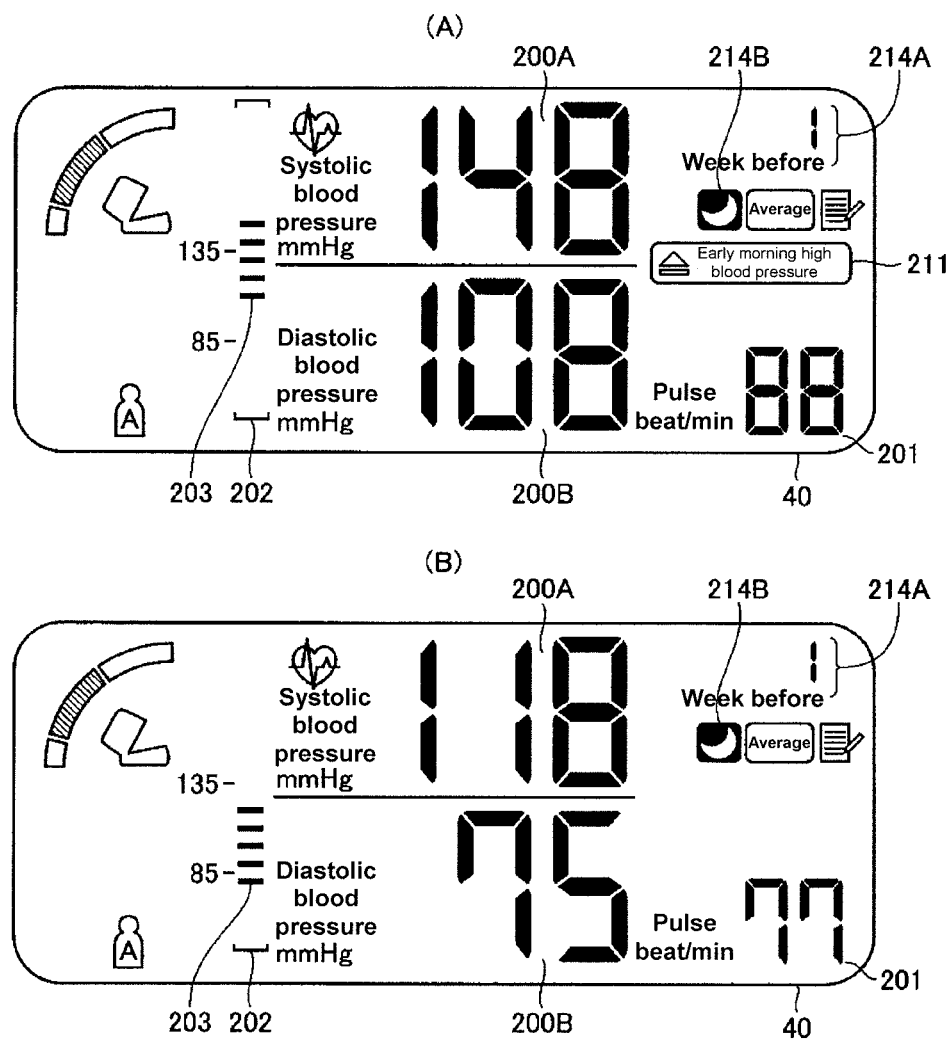
FIGS. 13A and 13B are views showing another further example of the display according to one or more embodiments of the present invention.

FIGS. 12A and 12B are screen examples of the callout and display of the average data of the morning time zone of one week before in step T7. In FIG. 12A, it is notified that the average data of the morning time zone of one week before corresponds to the category of "early morning high blood pressure" by the data 211, and notification is made that the average data does not correspond in FIG. 12B. In the screens of FIGS. 12A and 12B, it is indicated that the data is of one week before by the data 214A. FIGS. 13A and 13B are screen examples of the callout and display of the average data of the night time zone of one week before in step T19. In FIG. 13A, it is notified that the average data of the morning time zone of one week before corresponds to the category of "early morning high blood pressure" by the data 211, and notification is made that the average data does not correspond in FIG. 13B.

Figure 14:
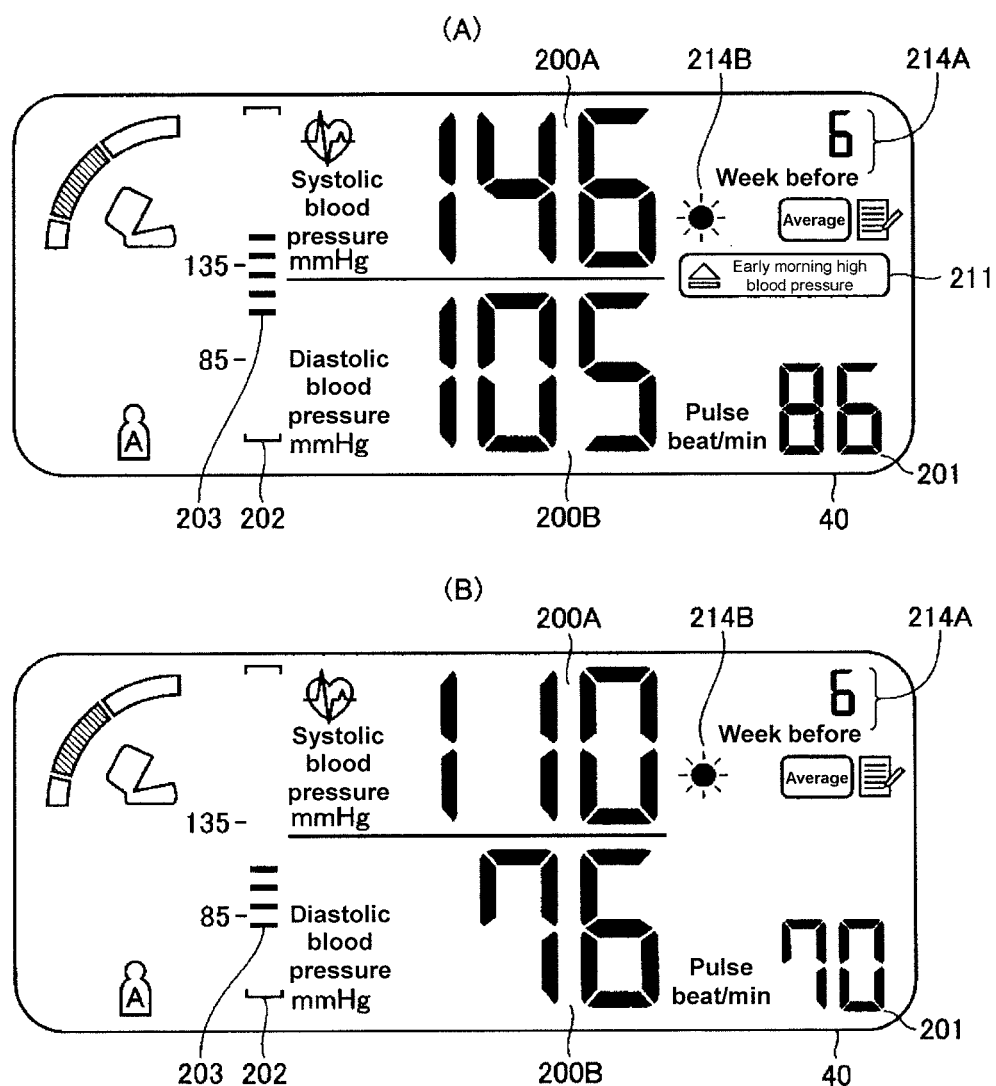
FIGS. 14A and 14B are views showing another further example of the display according to one or more embodiments of the present invention.
Figure 15:
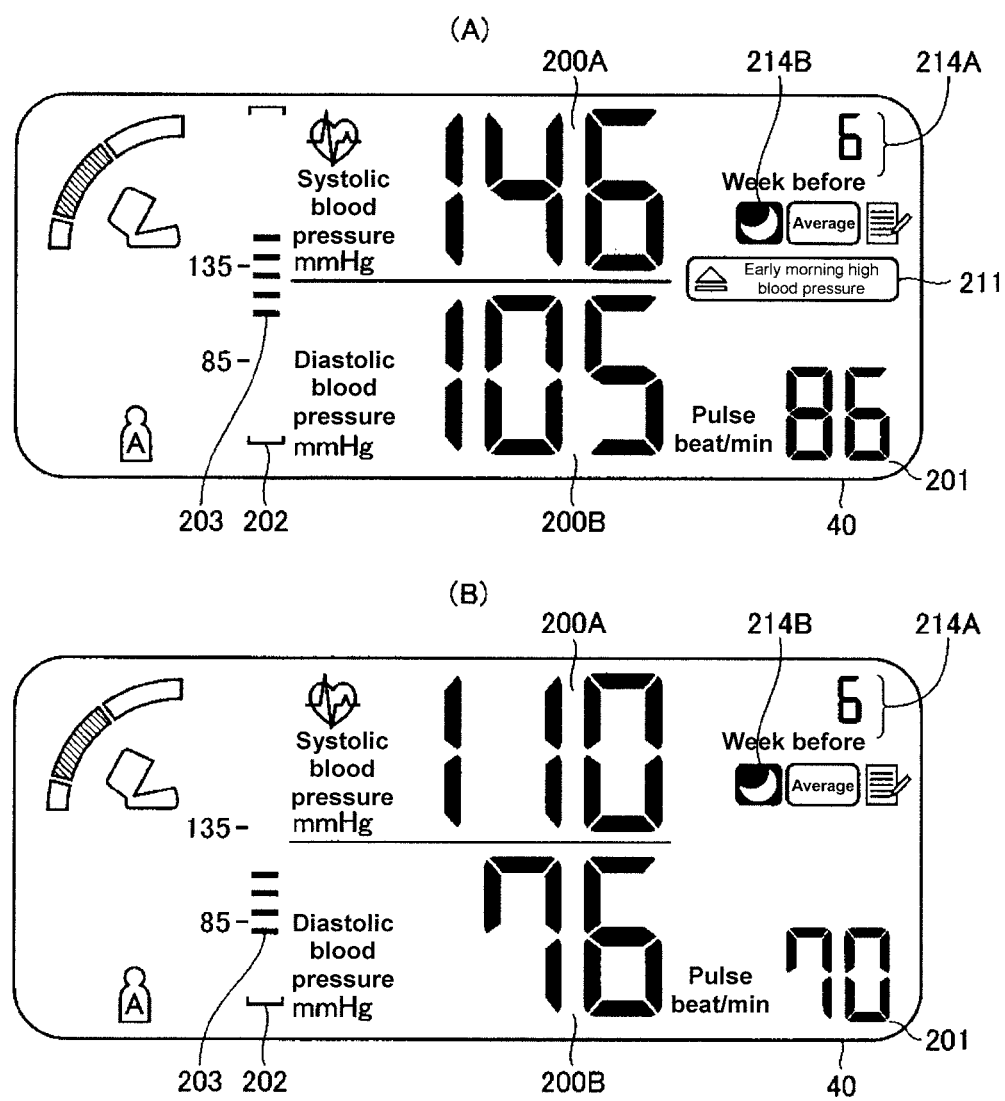
FIGS. 15A and 15B are views showing another further example of the display according to one or more embodiments of the present invention.

FIGS. 14A and 14B are screen examples of the callout and display of the average data of the morning time zone of six weeks before in step T7. It is indicated that the display data is of the average measurement data of six weeks before by the data 214A. FIGS. 15A and 15B are screen examples of the callout and display of the average data of the night time zone of six weeks before in step T19. Similar to FIG. 11B, in FIG. 15A, notification is made that the average data of the morning time zone of seven weeks before corresponds to the category of "early morning high blood pressure" by the data 211.

(Other Callout and Display Process)

The average calculating portion 1021 compares the calculated average measurement data ASYS and ADIA of the night time zone with the index data (135 mmHg/85 mmHg) of the high blood pressure, and detects whether or not corresponding to the category of the high blood pressure based on the comparison result. The data of the detection result is assumed to be stored in the record R3. Therefore, the every-week processing portion 114 can display the data indicating whether or not the average measurement data of the night time zone corresponds to the category of high blood pressure based on the relevant detection result in the callout and display of the record R3.

Figure 16:
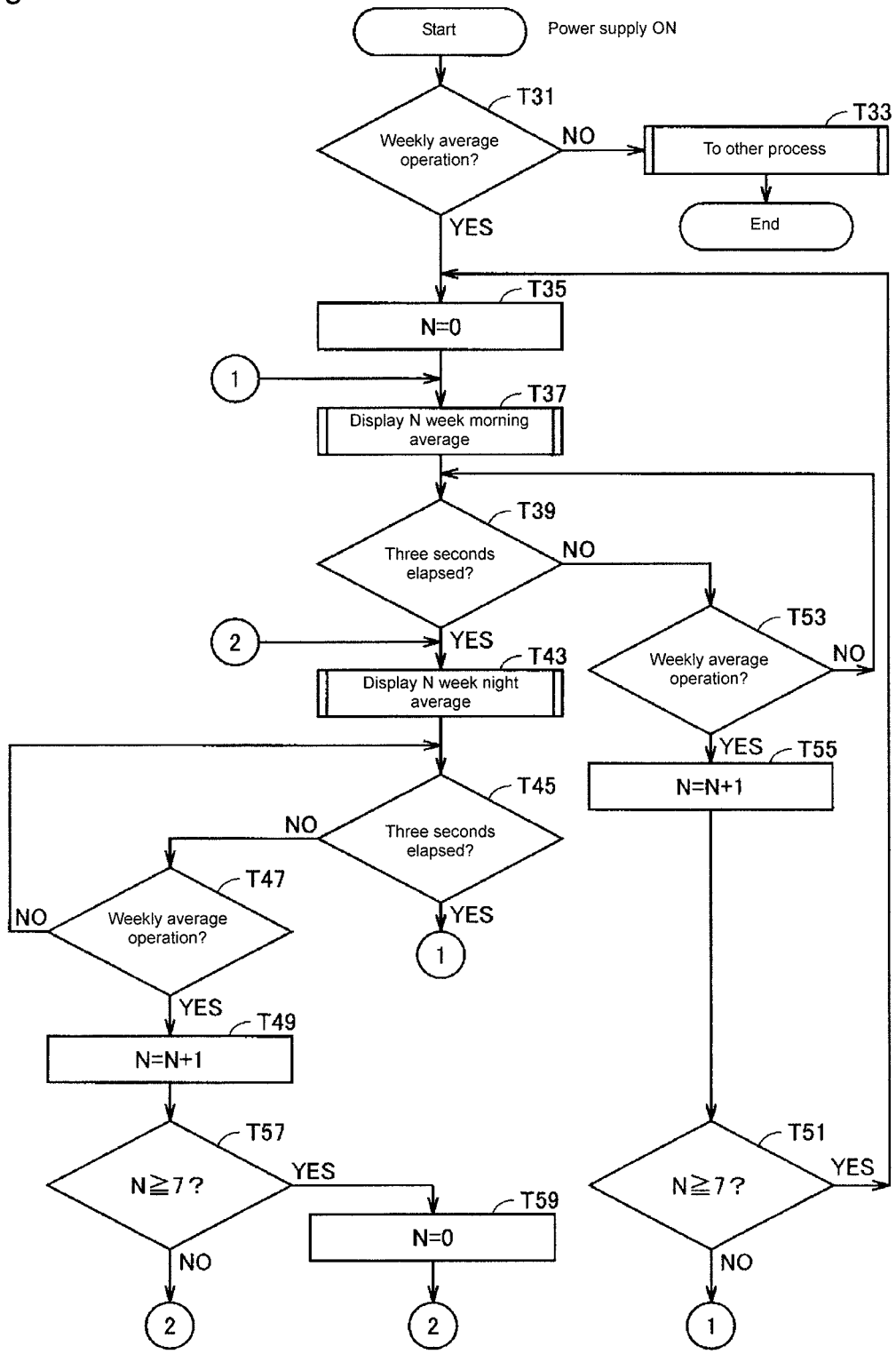
FIG. 16 is a flowchart showing another example of the callout and display process according to one or more embodiments of the present invention.

Another example of the callout and display process by the every-week processing portion 114 according to one or more embodiments of the present invention will be described with reference to the flowchart of FIG. 16. The program according to the flowchart of FIG. 16 is stored in a predetermined storage region of the memory 39. The following processes are realized when the CPU 30 reads out the program from the memory 39 and executes the read program.

In FIG. 16, assume that the switch 41A is operated and the power is supplied to each unit of the automatic winding electronic sphygmomanometer 1 (power supply ON). Assume that user A is selected. The processes of steps T31, T33, and T35 are carried out similar to the steps T1, T3, and T5 of FIG. 8.

In step T37, the every-week processing portion 114 calls out and displays the record R2 of the memory 39 pointed out by the pointer P2 having the value of the variable N. The average data of the morning time zone of this week (N=0) or N weeks before is thereby displayed. After the start of display, when determined that three seconds have elapsed without the switch 41D being operated (NO in step T53) based on the timing data of the timer 49 (YES in step T39), the process of step T43 is carried out.

In step T43, the every-week processing portion 114 calls out and displays the record R3 of the memory 39 pointed out by the pointer P3 having the value of the variable N. The average data of the night time zone of this week or N weeks before is thereby displayed. After the start of display, when determined that three seconds have elapsed without the switch 41D being operated (NO in step T47) based on the timing data of the timer 49 (YES in step T45), the process returns to step T37, and thereafter, the display returns to the display of the average data of the morning time zone of this week or N weeks before.

Figure 17:
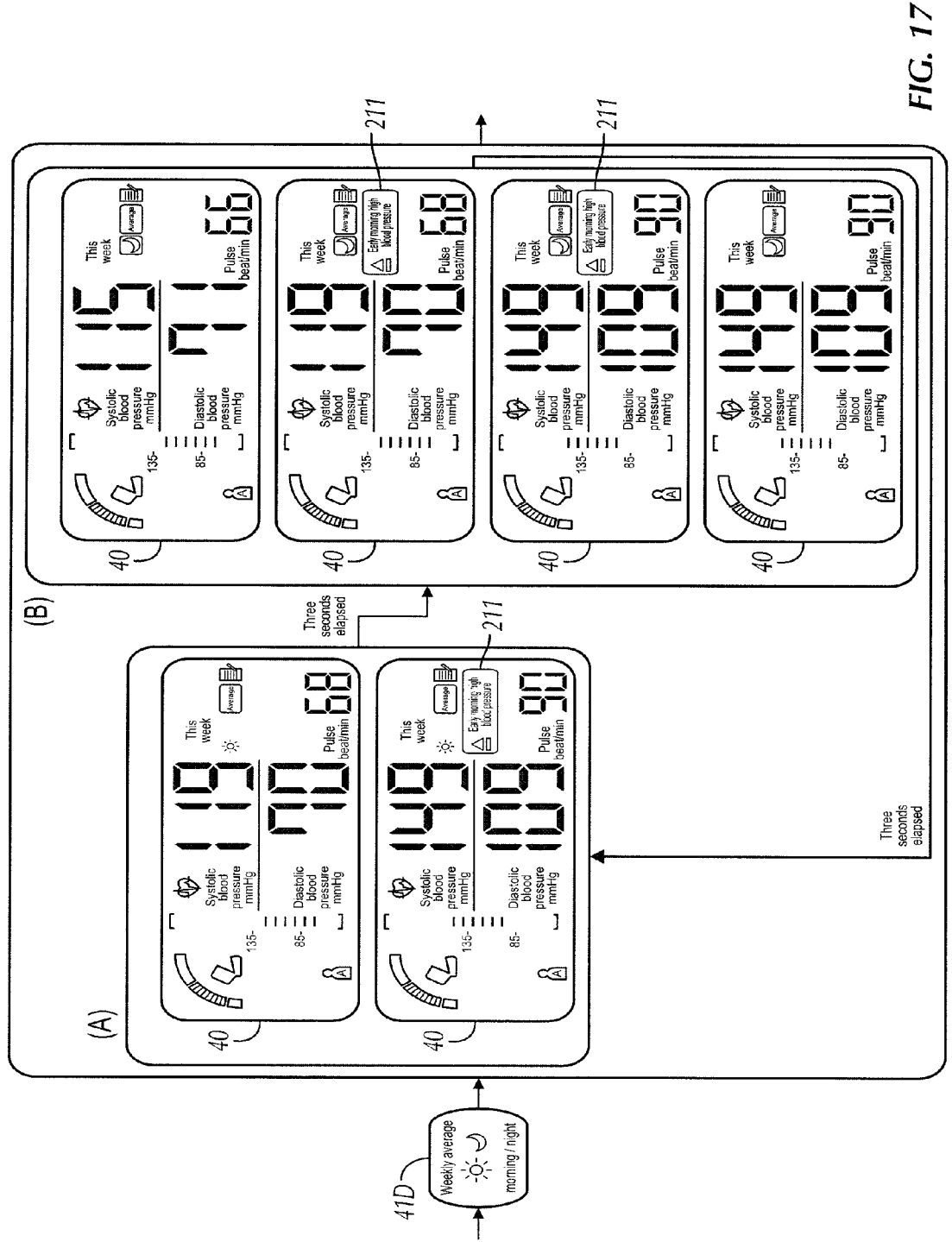
FIGS. 17A and 17B are views showing another further example of the display according to one or more embodiments of the present invention.
Figure 18:
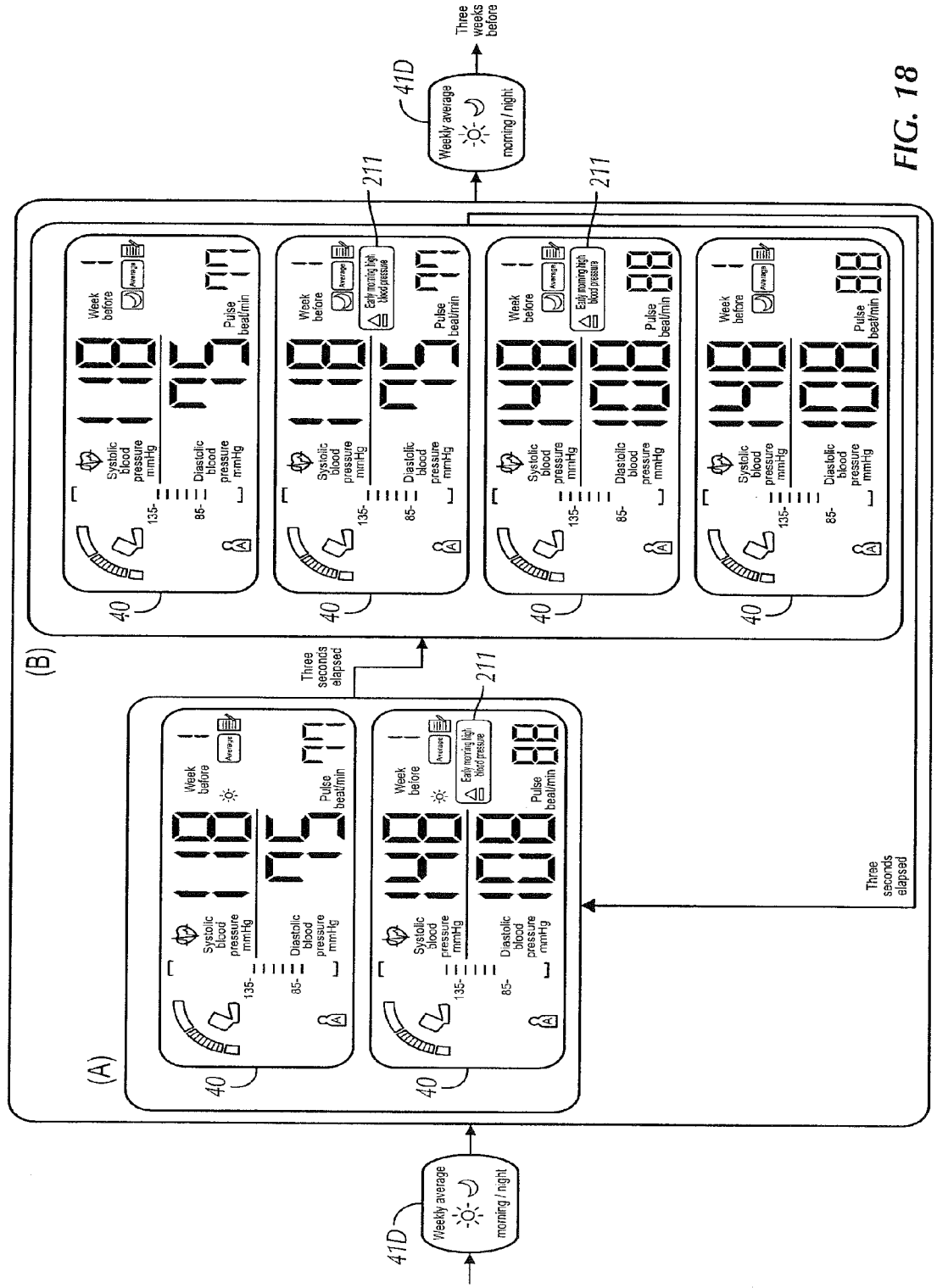
FIGS. 18A and 18B are views showing another further example of the display according to one or more embodiments of the present invention.

Therefore, unless the person to be measured performs some kind of operation after operating the switch 41D, the screen of the average data of the morning time zone of this week and the screen of the average data of the night time zone are alternately and automatically displayed at an interval of three seconds on the display unit 40 (see FIG. 17). Alternatively, the screen of the average data of the morning time zone of N weeks before and the screen of the average data of the night time zone are alternately and automatically displayed at an interval of three seconds (see FIG. 18).

FIG. 17A shows two display screen examples of the average data of the morning time zone of this week side by side. FIG. 17B shows a display screen example of the average data of the night time zone of this week alternately displayed with the screen of FIG. 17A. The screen at the upper level of FIG. 17A is a case where the blood pressure measurement data does not correspond to the category of the early morning high blood pressure, and the screen at the lower level is a case where the blood pressure measurement data corresponds to the relevant category. FIG. 17B shows four screens according to whether the average data of the night time zone of this week corresponds to the high blood pressure section (135 mmHg/85 mmHg) and whether the average data of the morning time zone of this week corresponds to the category of the early morning high blood pressure. The screen at the uppermost level shows a case where the blood pressure measurement data does not correspond to the high blood pressure section, and does not correspond to the category of early morning high blood pressure. The screen of the next level shows a case of corresponding only to the category of the early morning high blood pressure, and the screen of the next level shows a case of corresponding to the category of the early morning high blood pressure and the average data of the night time zone corresponding to the high blood pressure section. The screen at the lowermost level shows a case where the average data of the morning time zone does not correspond to the category of the early morning high blood pressure and the average data of the night time zone corresponds to the high blood pressure section. FIGS. 18A and 18B show a display screen example of the average data of the morning time zone one week before and a display screen example of the average data of the night time zone that are alternately and automatically displayed at an interval of three seconds, similar to FIGS. 17A and 17B.

In step T37 of the flowchart of FIG. 16, if the switch 41D is operated (step T37, NO in step T39, YES in step T53) before the elapse of three seconds after the start of display of the average data of the morning time zone, the variable N is updated +1 (step T55). The values of the pointers P2 and P3 are then updated to respectively point out the records R2 and R3 of the next order, and the screen is switched to the screen of the average data of the morning time zone of the week of the next order (see FIG. 17 or FIG. 18) for display while the condition of N≥7 is not satisfied (NO in step T51) (step T37). When the condition of N≥7 is satisfied (YES in step T51), the process is returned to step T35, and the callout and display process (step T35, step T37) on the record at the head is carried out. Thereafter, the subsequent processes are performed similar to the above.

Figure 19:
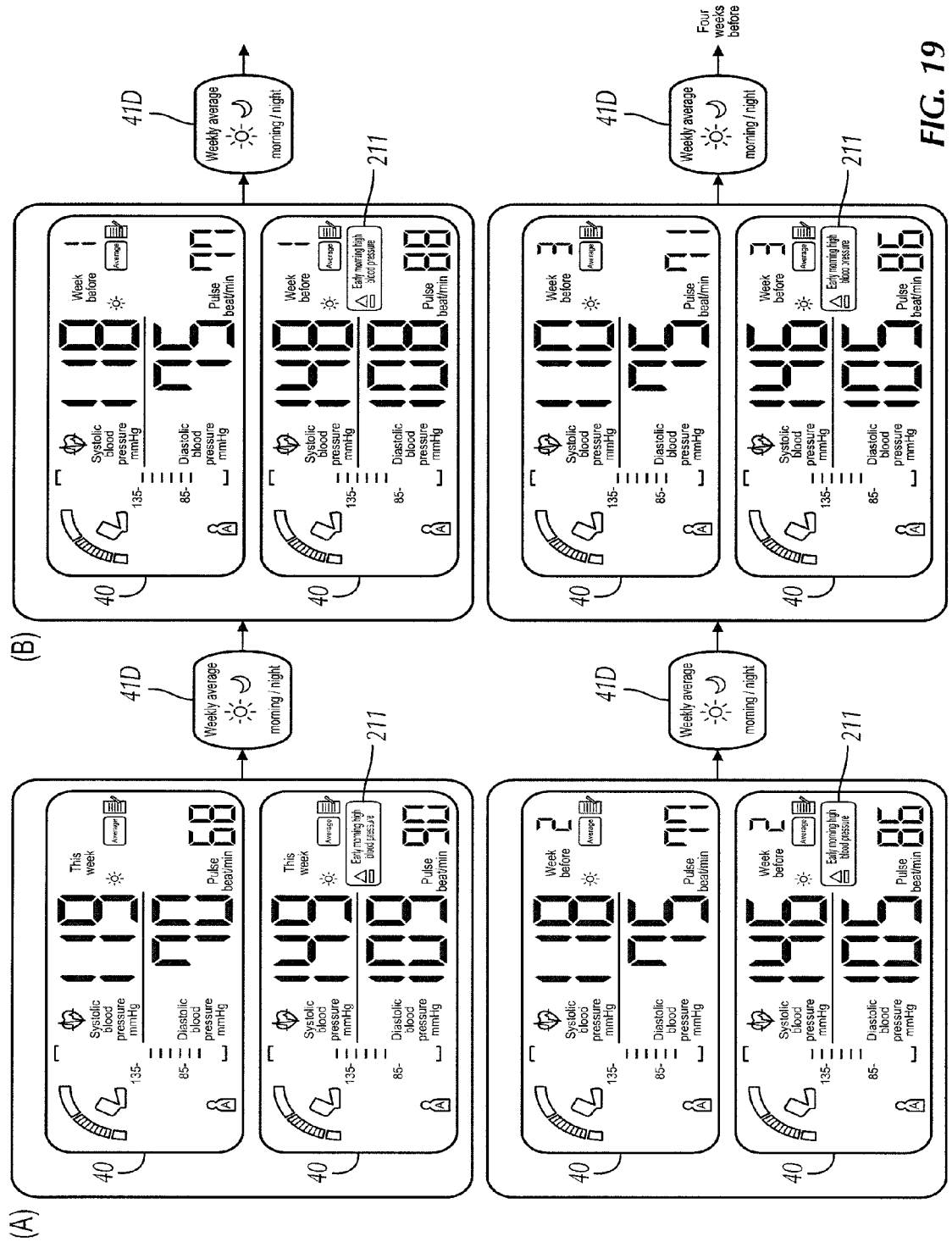
FIGS. 19A to 19D are views showing another further example of the display according to one or more embodiments of the present invention.

Therefore, every time the switch 41D is operated while displaying the screen of the average data of the morning time zone, the display screen can be continuously switched in order of average data of morning time zone of this week in FIG. 19A→average data of morning time zone of last week (one week before) in FIG. 19B→average data of morning time zone of week before last (two weeks before) in FIG. 19C→average data of morning time zone of three weeks before in FIG. 19D→average data of morning time zone of six weeks before→average data of morning time zone of this week in FIG. 19A. In FIGS. 19A to 19D, the display example of the average data not corresponding to the category of the early morning high blood pressure is shown at the upper level, and the display example of the average data corresponding to the category of the early morning high blood pressure is shown at the lower level.

Similarly, the display screen can be continuously switched to the display screen of the average data of the night time zone. Specifically, if the switch 41D is operated before an elapse of three seconds (NO in step T45, YES in step T47) after the start of display of the average data of the night time zone in step T43, the variable N is updated +1 (step T49). The values of the pointers P2 and P3 are then updated to respectively point out the records R2 and R3 of the next order. While the condition of (N≥7) is not satisfied (NO in step T57), the screen is switched to the screen of the average data of the night time zone of the week of the next order for display (step T43). If the condition of (N≥7) is satisfied (YES in step T51), the process is returned to step T35, and the callout and display process for the record at the head is carried out (step T35, step T37). The subsequent processes are performed similar to the above.

Figure 20:
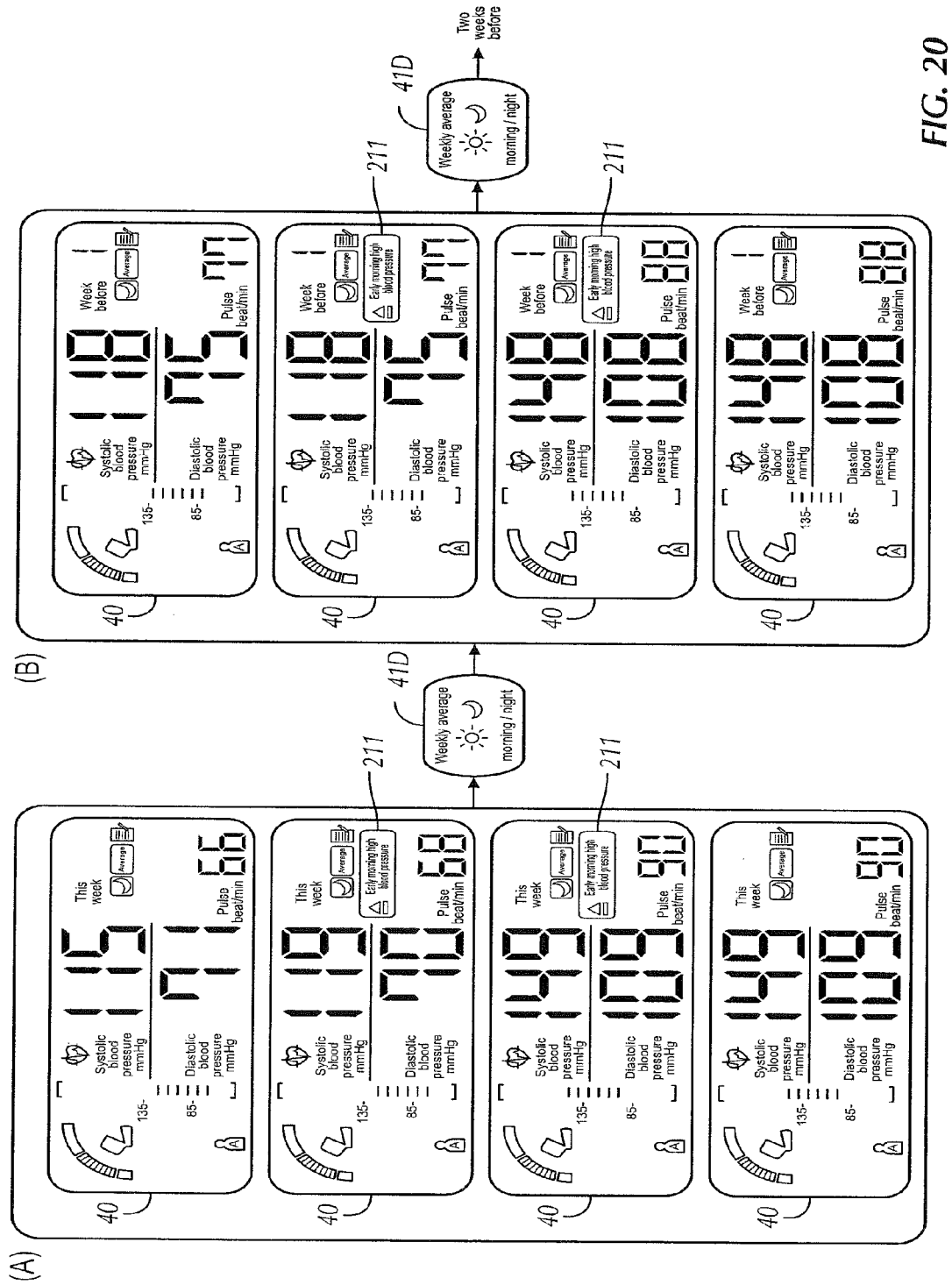
FIGS. 20A and 20B are views showing another further example of the display according to one or more embodiments of the present invention.
Figure 21:
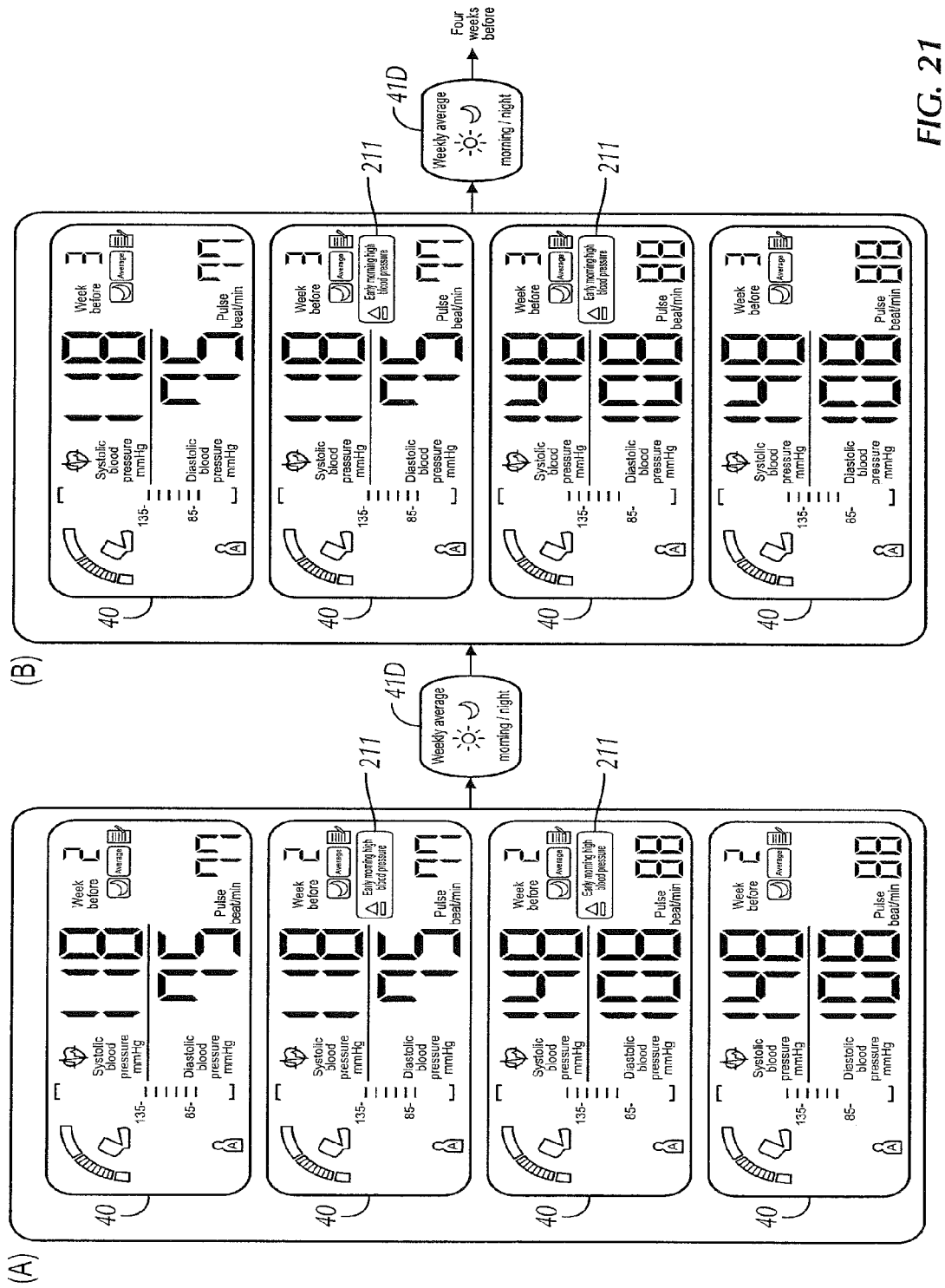
FIGS. 21A and 21B are views showing another further example of the display according to one or more embodiments of the present invention.

Therefore, every time the switch 41D is operated while displaying the screen of the average data of the night time zone, the display screen can be continuously switched in order of average data of night time zone of this week in FIG. 20A→average data of night time zone of last week (one week before) in FIG. 20B→average data of night time zone of week before last (two weeks before) in FIG. 21A→average data of night time zone of three weeks before in FIG. 21B→average data of night time zone of six weeks before→average data of night time zone of this week in FIG. 20A.

In each of FIGS. 20A and 20B and FIGS. 21A and 21B, the screen display examples are shown in four levels, but the screen of one of the levels is displayed on the display unit 40. Among the four levels, the first level shows an example where the average data of the night time zone does not correspond to the category of high blood pressure and the average data of the record R2 pointed out by the pointer P2, that is, the morning time zone of the corresponding week also does not correspond to the category of early morning high blood pressure. The second level shows an example where the average data of the night time zone does not correspond to the category of high blood pressure and only the average data of the record R2 pointed out by the pointer P2, that is, the morning time zone of the corresponding week corresponds to the category of early morning high blood pressure. The third level shows an example where the average data of the morning time zone corresponds to the category of early morning high blood pressure and the average data of the night time zone corresponds to the category of high blood pressure. The fourth level shows an example where only the average data of the night time zone corresponds to the category of high blood pressure.

When the average blood pressure value measured in the morning time zone of a certain week and the average blood pressure value measured in the night time zone of the corresponding week are alternately switched for display, the blood pressure value of the morning time zone and the blood pressure value of the night time zone are alternately switched for display at the same place on the screen, according to FIGS. 17A and 17B and FIGS. 18A and 18B. The change in blood pressure value thus can be easily checked.

In the callout and display process, the blood pressure value is simultaneously displayed with a numerical value on the same screen, and also displayed with an indicator by a bar graph of the blood pressure level bar 202. As a result, the user can easily visually recognize not only the change in blood pressure value but also the amount of change.

As described above, the person to be measured can compare the blood pressure values of the morning time zone and the night time zone without being conscious by automatically and alternately switching the display screens, so that the early morning high blood pressure can be easily found. Furthermore, the operation procedure is less because the operation button for displaying the respective blood pressure value is only one switch, the switch 41D, and hence, the operability can be enhanced and the manufacturing cost of the blood pressure measurement device can be suppressed as there is only one operation switch.

(Other Blood Pressure Measurement Devices)

Figure 22:
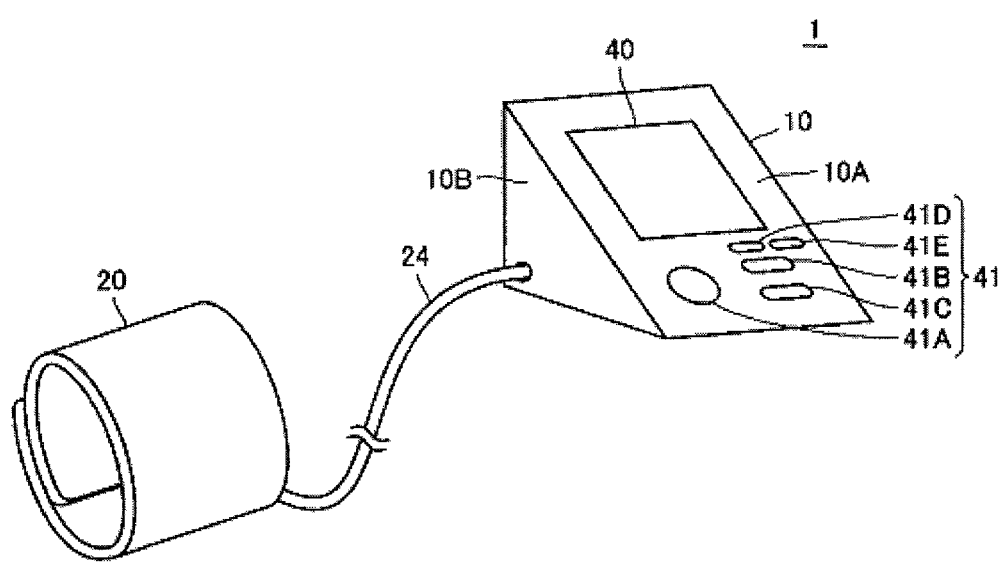
FIG. 22 is a schematic view of another blood pressure measurement device according to one or more embodiments of the present invention.

The blood pressure measurement device according to one or more embodiments of the present invention is not limited to an automatic winding type in which the main body and the cuff are integrally configured as shown in FIG. 1. As shown in FIG. 22, a blood pressure measurement device in which the cuff 20 to be wrapped around the measurement site by hand and the sphygmomanometer main body 10B are configured as separate bodies through an air tube 24 may be adopted. The operation unit 41 and the display unit 40 are arranged on the front surface 10A of the housing of the sphygmomanometer main body 10B.

Embodiments of the present invention are effective in a blood pressure measurement device for displaying data related to the blood pressure measurement of the morning time zone and the night time zone.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF REFERENCE NUMERALS 40 display unit
41 operation unit
101 pressure adjustment unit
102 blood pressure calculating unit
103 input determination unit
104 display processing unit
114 every-week processing portion
202 blood pressure level bar
203 mark
204 criterion value

The invention claimed is:

1. A blood pressure measurement device comprising:
a cuff to be attached to a measurement site of a living body;
a control unit that calculates a blood pressure while adjusting pressure of the cuff for blood pressure measurement;
a storage unit that stores morning blood pressure data for a plurality of days measured in a time zone corresponding to morning, and night blood pressure data for a plurality of days measured in a time zone corresponding to night calculated by the control unit;
a display unit;
a display operation unit having a single switch manually operated by a user to control the display unit;
a display processing unit that reads out data from the storage unit and displays the read data on the display unit; and
a central processing unit (CPU) that controls the control unit, the storage unit, the display unit and the display processing unit,
wherein the display processing unit calculates, by a control of the CPU, an average of the morning blood pressure data of each week for a plurality of weeks,
wherein the display processing unit calculates, by the control of the CPU, an average of the night blood pressure data of each week for a plurality of weeks,
wherein the display processing unit provides a first instruction to the display unit to display, by the control of the CPU, alternately with a first predetermined time interval, the average of the morning blood pressure data and the average of the night blood pressure data both belonging to one predetermined week,
wherein, in response to a manual operation of the single switch at a time when the average of the morning blood pressure data of said one predetermined week is being displayed by the display unit, the display processing unit provides a second instruction to the display unit to display, by the control of the CPU, alternately with a second predetermined time interval, and starting from the average of the morning blood pressure data of a week that is one week next to said one predetermined week, the average of the morning blood pressure data belonging to the week that is next to said one predetermined week, and the average of the night blood pressure data belonging to the week that is one week next to said one predetermined week, and
wherein, in response to a manual operation of the single switch at a time when the average of the night blood pressure data of said one predetermined week is being displayed by the display unit, the display processing unit provides a third instruction to the display unit to display, by the control of the CPU, alternately with a predetermined time interval, and starting from the average of the night blood pressure data of the week that is one week next to said one predetermined week, the average of the night blood pressure data belonging the week that is next to said one predetermined week, and the average of the morning blood pressure data both belonging to the week that is one week next to said one predetermined week.

2. The blood pressure measurement device according to claim 1, wherein the display processing unit displays, by the control of the CPU, information indicating that a blood pressure value of the average of the morning blood pressure data belonging to the week that is next to said one predetermined week corresponds to a category of early morning high blood pressure on a same screen as a display screen of the average of the morning blood pressure data belonging to the week that is next to said one predetermined week when displaying the average of the morning blood pressure data belonging to the week that is next to said one predetermined week.

3. The blood pressure measurement device according to claim 2, wherein the display processing unit displays, by the control of the CPU, information indicating that the blood pressure value of the average of the morning blood pressure data belonging to the week that is next to said one predetermined week corresponds to the category of early morning high blood pressure on the same screen as a display screen of the average of the night blood pressure data belonging to the week that is next to said one predetermined week when displaying the average of the night blood pressure data belonging to the week that is next to said one predetermined week.

4. The blood pressure measurement device according to claim 1, wherein the display processing unit displays, by the control of the CPU, a blood pressure indicated by the average of the morning blood pressure data or the average of the night blood pressure data with a rectangular bar sectionalized by a plurality of segments of a predetermined unit, and simultaneously, with a numerical value in the same screen of the display unit.

5. The blood pressure measurement device according to claim 4, wherein, by control of the CPU, a criterion value indicating the predetermined blood pressure section is displayed in association at a position indicating a blood pressure value corresponding to the criterion value on the bar.

6. The blood pressure measurement device according to claim 1,
wherein the storage unit further stores a detection result of whether the average of the morning blood pressure data corresponds to a category of early morning high blood pressure based on a comparison between the average of the morning blood pressure data belonging to a week that is one week next to said one predetermined week and an index of predetermined data characteristic of high blood pressure, and
wherein when the detection result corresponds to the category of early morning high blood pressure, the display unit displays, by control of the CPU, an indicator of the detection result simultaneously with the average of the night blood pressure data belonging to the week that is one week next to said one predetermined week during the alternate display of the average of the morning blood pressure data and the average of the night blood pressure data belonging to the week that is one week next to said one predetermined week.

7. The blood pressure measurement device according to claim 1, wherein the display processing unit provides a fourth instruction to the display unit to display, by control of the CPU, a week indicator showing a number of weeks prior to said one predetermined week.

* * * * *